(12) United States Patent
Ordentlich et al.

(10) Patent No.: US 12,168,054 B2
(45) Date of Patent: Dec. 17, 2024

(54) METHOD OF TREATING CANCER USING A COMBINATION OF ENTINOSTAT AND AN ANTI-CSF-1R ANTIBODY

(71) Applicant: SYNDAX PHARMACEUTICALS, INC., Waltham, MA (US)

(72) Inventors: Peter Ordentlich, Lexington, MA (US); Lei Wang, Waltham, MA (US)

(73) Assignee: Syndax Pharmaceuticals, Inc., Waltham, MA (US)

( * ) Notice: Subject to any disclaimer, the term of this patent is extended or adjusted under 35 U.S.C. 154(b) by 237 days.

(21) Appl. No.: 16/614,863

(22) PCT Filed: May 18, 2018

(86) PCT No.: PCT/US2018/033324
§ 371 (c)(1),
(2) Date: Nov. 19, 2019

(87) PCT Pub. No.: WO2018/213665
PCT Pub. Date: Nov. 22, 2018

(65) Prior Publication Data
US 2020/0171150 A1   Jun. 4, 2020

Related U.S. Application Data

(60) Provisional application No. 62/508,842, filed on May 19, 2017.

(51) Int. Cl.
| A61K 39/395 | (2006.01) |
| A61K 9/00 | (2006.01) |
| A61K 31/4406 | (2006.01) |
| A61K 39/00 | (2006.01) |
| A61P 35/00 | (2006.01) |
| C07K 16/28 | (2006.01) |

(52) U.S. Cl.
CPC ...... *A61K 39/39541* (2013.01); *A61K 9/0053* (2013.01); *A61K 31/4406* (2013.01); *A61P 35/00* (2018.01); *C07K 16/2866* (2013.01); *A61K 2039/505* (2013.01); *A61K 2039/545* (2013.01); *C07K 2317/24* (2013.01); *C07K 2317/565* (2013.01); *C07K 2317/76* (2013.01); *C07K 2317/92* (2013.01)

(58) Field of Classification Search
CPC ........... A61P 35/00; C07K 16/2866; C07K 2317/565; C07K 2317/76; C07K 2317/92; A61K 2039/505; A61K 2039/545
See application file for complete search history.

(56) References Cited

U.S. PATENT DOCUMENTS

| 8,017,739 B2 | 9/2011 | Eichner et al. |
| 8,500,712 B2 | 8/2013 | Polettini et al. |
| 8,652,469 B2 | 2/2014 | Kavanaugh et al. |
| 9,908,939 B2 | 3/2018 | Craggs et al. |
| 10,226,472 B2 | 3/2019 | Goodenow et al. |
| 10,421,814 B2 | 9/2019 | Craggs et al. |
| 11,324,822 B2 | 5/2022 | Goodenow et al. |
| 11,397,184 B2 | 7/2022 | Ordentlich |
| 2007/0086979 A1 | 4/2007 | Chevrier et al. |
| 2009/0048156 A1 | 2/2009 | Brodie et al. |
| 2009/0148905 A1 | 6/2009 | Ashman et al. |
| 2009/0149511 A1 | 6/2009 | Burk et al. |
| 2010/0092992 A1 | 4/2010 | Hornbeck et al. |
| 2010/0305167 A1 | 12/2010 | Burk et al. |
| 2011/0178278 A1 | 7/2011 | Haegel et al. |
| 2012/0070461 A1 | 3/2012 | Singh et al. |
| 2012/0276004 A1 | 11/2012 | Epstein et al. |
| 2013/0095098 A1 | 4/2013 | Tyson |
| 2013/0150386 A1 | 6/2013 | Goodenow et al. |
| 2014/0378420 A1 | 12/2014 | Goodenow et al. |
| 2016/0067336 A1 | 3/2016 | Fandi et al. |
| 2016/0108123 A1 | 4/2016 | Freeman et al. |
| 2016/0200820 A1 | 7/2016 | Marshall |
| 2017/0049755 A1 | 2/2017 | Villagra et al. |
| 2017/0189526 A1 | 7/2017 | Zhou et al. |
| 2018/0078639 A1 | 3/2018 | Goodenow et al. |
| 2018/0252721 A1 | 9/2018 | Ordentlich |
| 2018/0353602 A1 | 12/2018 | Goodenow et al. |
| 2021/0239697 A1 | 8/2021 | Ordentlich et al. |
| 2023/0022573 A1 | 1/2023 | Goodenow et al. |
| 2023/0061048 A1 | 3/2023 | Ordentlich |

FOREIGN PATENT DOCUMENTS

| AR | 079333 A1 | 1/2012 |
| CN | 105492007 A | 4/2016 |
| WO | WO-03080672 A1 | 10/2003 |
| WO | WO-2007143146 A2 | 12/2007 |

(Continued)

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Guerriero JL, et al. (2016) Cancer Immunol Res (2016) 4 (11_Supplement): B038. (https://doi.org/10.1158/2326-6066.IMM2016-B038).*
Bauer S. et al. "Phase I study of panobinostat and imatinib in patients with treatment-refractory metastatic gastrointestinal stromal tumors", British Journal of Cancer, 2014, vol. 110, No. 5, pp. 1155-1162.

(Continued)

*Primary Examiner* — Robert S Landsman
(74) *Attorney, Agent, or Firm* — COOLEY LLP; Heidi A. Erlacher; Eric A. Owens

(57) ABSTRACT

The present disclosure relates to a combination of an anti-CSF-1R antibody or anti-CSF-1 antibody or antigen binding fragment thereof or an inhibitor of CSF-1R activity and an HDAC inhibitor, e.g., entinostat, and methods of using the combination for administering to subjects in need thereof for the treatment of cancer.

22 Claims, 5 Drawing Sheets

Specification includes a Sequence Listing.

(56) References Cited

FOREIGN PATENT DOCUMENTS

| WO | WO-2008055013 A2 | 5/2008 |
|---|---|---|
| WO | WO 2009/026303 A1 | 2/2009 |
| WO | WO-2009092237 A1 | 7/2009 |
| WO | WO 2009/112245 A1 | 9/2009 |
| WO | WO-2010012667 A1 | 2/2010 |
| WO | WO 2011/070024 A1 | 6/2011 |
| WO | WO 2011/107553 A1 | 9/2011 |
| WO | WO 2011/123381 A1 | 10/2011 |
| WO | WO 2011/131407 A1 | 10/2011 |
| WO | WO 2011/140249 A2 | 11/2011 |
| WO | WO-2012082689 A1 | 6/2012 |
| WO | WO-2012110360 A1 | 8/2012 |
| WO | WO-2013033656 A1 | 3/2013 |
| WO | WO-2013057281 A2 | 4/2013 |
| WO | WO 2013/068902 A1 | 5/2013 |
| WO | WO-2013087699 A1 | 6/2013 |
| WO | WO-2013119716 A1 | 8/2013 |
| WO | WO 2013/132044 A1 | 9/2013 |
| WO | WO-2014011713 A2 | 1/2014 |
| WO | WO-2014036076 A1 | 3/2014 |
| WO | WO-2014085461 A1 | 6/2014 |
| WO | WO-2014194280 A2 | 12/2014 |
| WO | WO-2015016718 A1 | 2/2015 |
| WO | WO 2015/028455 A1 | 3/2015 |
| WO | WO-2015028454 A2 | 3/2015 |
| WO | WO-2015035112 A1 | 3/2015 |
| WO | WO-2016010879 A1 | 1/2016 |
| WO | WO 2016/128318 A1 | 8/2016 |
| WO | WO-2016154068 A1 | 9/2016 |
| WO | WO-2017004092 A1 | 1/2017 |
| WO | WO-2017041043 A1 | 3/2017 |
| WO | WO-2018213665 A1 | 11/2018 |

OTHER PUBLICATIONS

Bourette et al. "Early Events in M-CSF Receptor Signaling", Growth Factors, 2000, vol. 17, p. 155-166.
Cohen et al. "Targeting BCL6-Mediated Resistance to BCR-ABL Targeted Tyrosine Kinase Inhibitors (TKIs) in Philadelphia Chromosome Positive Acute Lymphoblastic Leukemia (Ph+ALL) through the Addition of Histone Deacetylase (HDAC) Inhibitors", Blood, 2015, vol. 126, No. 23, p. 1277-1279.
Guerriero et al.,"Class IIa HDAC inhibition reduces breast tumours and metastases through anti-tumour macrophages", Nature, 2017, vol. 543, p. 428-432.
Husson et al. "CSF-1 stimulation induces the formation of a multiprotein complex including CSF-1 receptor, c-Cbl, PI 3-kinase, Crk-II and Grb2", Oncogene,1997, vol. 14, p. 2331-2338.
Mashkani et al. "Colony stimulating factor-1 receptor as a target for small molecule inhibitors", Bioorganic & Medicinal Chemistry, 2010, vol. 18, p. 789-1797.
Mok et al. "Inhibition of CSF-1 Receptor Improves the Antitumor Efficacy of Adoptive Cell Transfer Immunotherapy", Mol Cancer Research 2014, vol. 74, No. 1, p. 153-161.
Mottamal et al. "Histone Deacetylase Inhibitors in Clinical Studies as Templates for New Anticancer Agents", Molecules, 2015, vol. 20, No. 3, pp. 3898-3941.
Patel et al. "Colony-Stimulating Factor-1 Receptor Inhibitors for the Treatment of Cancer and Inflammatory Disease", Current Topics in Medicinal Chemistry, 2009, vol. 9, p. 599-610.
Ramachandran et al. "Design, synthesis and optimization of bis-amide derivatives as CSF1R inhibitors", Bioorganic & Medicinal Chemistry Letters, 2017, vol. 27, No. 10, p. 2153-2160.
Sherr C.J. et al. "Inhibition of Colony-Stimulating Factor-i Activity by Monoclonal", Blood, 1989, vol. 73, No. 7, p. 1786-1793.
Suzu et al. "Biologic Activity of Proteoglycan Macrophage Colony-Stimulating Factor", Joural of Immunology, 1997, vol. 159, p. 1860-1867.
Yeung et al. "Colony-stimulating Factor-1 Stimulates the Formation of Multimeric Cytosolic Complexes of Signaling Proteins and Cytoskeletal Componenets in Macrophages", 2003, The Journal of Biological Chemistry, 1998, vol. 273, No. 27, p. 17128-17137.
Yeung et al. "Proteomic Approaches to the Analysis of Early Events in Colony-stimulating Factor-1 Signal Transduction", Molecular & Cellular Proteomics, 2003, p. 1143-1155.
Yu et al. "CSF-1 receptor structure/function in MacCsf1r−/−macrophages: regulation of proliferation, differentiation, and morphology", Journal of Leukocyte Biology, 2008, vol. 84, p. 852-863.
Ang Huang et al. "Increased CD14+HLA-DR-/low myeloid-derived suppressor cells correlate with extrathoracic metastasis and poor response to chemotherapy in non-small cell lung cancer patients", Cancer Immunology, Immunotherapy, vol. 62, No. 9, 1 2013, pp. 1439-1451.
Azad, N. et al. "The future of epigenetic therapy in solid tumours—lessons from the past", Nature Reviews, Clinical Oncology, (2013); 10:256-266.
Bergenfelz, C., et al., "Systemic Monocytic-MDSCs Are Generated from Monocytes and Correlate with Disease Progression in Breast Cancer Patients," PLoS One, May 20, 2015, vol. 10(5), pp. 1-23.
Brahmer, Jr. et al.; Immune Checkpoint Inhibitors: Making Immunotherapy a Reality for the Treatment of Lung Cancer. Cancer Immunol Res, (2013); 1(2):85-91.
Carter, C. A. et al. "Addressing the elephant in the room, therapeutic resistance in nonsmall cell lung cancer, with epigenetic therapies", Oncotarget, (2016), 7(26):40781-40791.
Chien et al. "Platinum-Sensitive Recurrence in Ovarian Cancer: the Role of Tumor Microenvironment", Frontiers in Oncology, (Sep. 24, 2013); 3(251):1-6.
Clinical Trial NCT02437136, "Ph1b/2 Dose-Escalation Study of Entinostat With Pembrolizumab in NSCLC With Expansion Cohorts in NSCLC and Melanoma", SNDX-275-0601, (May 4, 2015), 16 pages.
De Felice et al. "Immunotherapy of Ovarian Cancer: the Role of Checkpoint Inhibitors", Journal of Immunology Research, (2015); 2015(191832):1-8.
Department of Health & Human Services; Premarket Approval Letter From the Center for Devices and Radiological Health (CDRH) of the Food and Drug Administration, (FDA); Filed: Apr. 6, 2015, 4 pages.
"ESMO 2014: Results of a Phase III Randomised Study of Nivolumab in Patients with Advanced Melanoma After Prior Anti-CTLA4 Therapy", European Society for Medical Oncology, Sep. 29, 2014 URL: http://www.esmo.org/Conferences/Past-Conferences/ESMO-2014-Congress/News-Articles/Results-of-a-Phase-III-Randomised-Study-of-Nivolumab-in-Patients-with-Advanced-Melanoma-After-Prior-Anti-CTLA4-Therapy, (Sep. 2014), 3 pages.
Exhibit A: European Office Action for Application No. EP18733390 dated Feb. 9, 2022; 9 pages.
Forde, P. M. et al. "New strategies in lung cancer: epigenetic therapy for non-small cell lung cancer", Clinical Cancer Research, (2014); 20(9):2244-2248.
Frys et al., "Entinostat, a novel histone deacetylase inhibitor is active in B-cell lymphoma and enhances the anti-tumour activity of rituximab and chemotherapy agents", British Journal of Haematology, (2015); 169:506-519.
Garon E. et al. "Preliminary clinical safety and activity of MK-3475 monotherapy for the treatment of previously treated patients with non-small cell lung cancer (NSCLC)", Journal of Thoracic Oncology, (2013), 8(Suppl. 2):S364-S365.
Gore, L., et al., "A phase I and pharmacokinetic study of the oral histone deacetylase inhibitor, MS-275, in patients with refractory solid tumors and lymphomas," Clinical cancer research, Jul. 15, 2008, vol. 14(14), pp. 4517-4525.
International Search Report and Written Opinion of International Application No. PCT/EP2014/068047, dated Mar. 30, 2015, 19 pages.
International Search Report and Written Opinion of International Application No. PCT/EP2014/068050, dated Nov. 6, 2014, 13 pages.
International Search Report and Written Opinion of International Application No. PCT/EP2016/052494, dated Apr. 5, 2016, 11 pages.

(56) References Cited

OTHER PUBLICATIONS

International Search Report and Written Opinion of International Application No. PCT/US2012/053551, dated Feb. 1, 2013, 11 pages.
International Search Report and Written Opinion of International Application No. PCT/US2016/023298, dated Aug. 11, 2016, 11 pages.
International Search Report and Written Opinion of International Application No. PCTU.S. Pat. No. 2016039906, dated Sep. 22, 2016, 11 pages.
International Search Report and Written Opinion of International Application No. PCT/US2016/050274, dated Feb. 1, 2017, 14 pages.
International Search Report and Written Opinion of International Application No. PCT/US2016/068836, dated Mar. 27, 2017, 10 pages.
International Search Report and Written Opinion of International Application No. PCT/US2019/031210, dated Sep. 20, 2019, 16 pages.
Kim et al. "Eradication of metastatic mouse cancers resistant to immune checkpoint blockade by suppression of myeloid-derived cells". Proceedings of the National Academy of Sciences, (2014); 111(32):11774-11779.
Kukushkina M.N. et al. "Tumors of the skin, soft tissues, bones", National Cancer Institute, Kyiv, (2014); 4(16):6-11. (English machine ~translation included).
Lee et al. "Patients [Pts] with advanced NSCLC from Korea treated with pembrolizumab (Pembro) in Keynote-001", Annals of Oncology, (2015); 26(suppl. 9):p. 461.
Lim et al. "Antibody blockade of c-fms suppresses the progression of inflammation and injury in early diabetic nephropathy in obese db/db mice", Diabetologia; (May 23, 2009); 52(8):1669-1679.
Lin, Y. et al. "Immunosuppressive CD14HLA-DRlow/ monocytes in B-cell non-Hodgkin lymphoma," Blood, (Jan. 20, 2011); 117(3):872-881.
Linares et al. "Manipulating Protein Acetylation in Breast Cancer: a promising approach in combination with hormonal therapies", Journal of Biomedicine and Biotechnology, (2010); 2011:1-15. DOI: http://dx.doi.org/10.1155/2011/856985.
Longoria, C et al. "Immune Checkpoint Inhibition: Therapeutic Implications in Epithelial Ovarian Cancer", Recent Patents on Anti-Cancer Drug Discovery, (2015); 10(2):1-12.
Lustberg et al., Epigenetic therapy in breast cancer. Curr. Breast Cancer Report, 3:34-43 (2011) Published online Dec. 22, 2010.
Luvero, D et al. "Treatment Options in Recurrent Ovarian Cancer: Latest Evidence and Clinical Potential", Therapeutic Advances in Medical Oncology, (2014); 6(5):229-239.
MacDonald et al. "An antibody against the colony-stimulating factor 1 receptor depletes the resident subset of monocytes and tissue- and tumor-associated macrophages but does not inhibit inflammation", Blood, American Society of Hematology, (Nov. 11, 2010), 116(19):3955-3963.
Mahoney et al., "Prognostic and Predictive Markers for the New Immunotherapies", Oncology, (2014); 28(3):1-10.
Maurer et al. "Emerging targeted therapies in scleroderma lung and skin fibrosis", Bailliere's Best Practice and Research Clinical Reumatology, (2011); 25(6):843-858.
McDermott, J., et al., "Pembrolizumab: PD-1 inhibition as a therapeutic strategy in cancer", Drugs of Today, (2015); 51(1):7-20.
Moreno et al. "Anti-Programmed Cell Death Protein-1/Ligand-1 Therapy in Different Cancers", British Journal of Cancer, (Apr. 28, 2015); 112(9):1421-1427.
Ngamphaiboon, N et al. "A Phase I Study of the Histone Deacetylase (HDAC) Inhibitor Entinostat, in Combination with Sorafenib in Patients with Advanced Solid Tumors", Investigational New Drugs, (Nov. 5, 2014); 33(1):225-232.
Orillion et al. "Entinostat Neutralizes Myeloid-Derived Suppressor Cells and Enhances the Antitumor Effect of PD-1 Inhibition in Murine Models of Lung and Renal Cell Carcinoma", Clinical Cancer Research, (2017); 23(17):5187-5201.
Paulus et al. "Colony-Stimulating Factor-1 Antibody Reverses Chemoresistance in Human MCF-7 Breast Cancer Xenografts", Cancer Research, (Apr. 15, 2006); 66(8):4349-4356.
Rudolph et al, "Increased frequencies of CD11b+ CD33+CD14+ HLA-DRlow myeloid-derived suppressor cells are an early event in melanoma patients", Experimental Dermatology, (2014), 23:199-218.
Spigel, DR et al. "Clinical Activity, Safety, and Biomarkers of MPDL3280A, an Engineered PD-L1 Antibody in Patients With Locally Advanced or Metastatic Non-Small Cell Lung Cancer (NSCLC)", J. Clin. Oncol., (2013); 31(Suppl):Abstr 8008., 4 pages.
Suraweera et al. "Combination Therapy With Histone Deacetylase Inhibitors (HDACi) for the Treatment of Cancer: Achieving the Full Therapeutic Potential of HDACi", Frontiers in Oncology, (Mar. 29, 2018); 8(92):1-15.
Syndax Pharmaceuticals et al. "Syndax Announces Updated Results from Phase 2 Encore 601 Trial of Entinostat in Combination with Keytruda (pembrolizumab)", (2018); 5 pages. Retrieved from the Internet: URL:https://www.prnewswire.com/news-releases/syndax-announcesupdated-results-from-phase-2-encore-601-trial-of-entinostat-incombination- with-keytruda-pembrolizumab-300650233.html.
Thurn, K.T. et al., "Rational Therapeutic Combinations with Histone Deacetylase Inhibitors for the Treatment of Cancer", Future Oncology, (2011); 7(2):1-34.
Vetsika, E. et al. "A Circulating Subpopulation of Monocytic Myeloid-Derived Suppressor Cells as an Independent Prognostic/ Predictive Factor in Untreated Non-Small Lung Cancer Patients", Journal of Immunology Research, (2014); 2014(659294):12 pages.
Weintraub, K. "Take two: Combining immunotherapy with epigenetic drugs to tackle cancer", Nature Medicine, (2016); 22(1):8-10.
Woods, D. M., et al., "Abstract 4090: Inhibition of class I histone deacetylases promotes robust and durable enhancement of PDL1 expression in melanoma: Rationale for combination therapy," Cancer Research, (Oct. 2014); 74(Supp 19):4090. 1 page.
Wrangle et al. "Alterations of immune response of non-small cell lung cancer with Azacytidine", Oncotarget, (2013); 4(11): 2067-2079.
Yardley, DA et al.; "A Randomized, Phase 2, Double-Blind, Placebo-Controlled Study of Exemestane With or Without Entinostat (SNDX-275) in Postmenopausal Women With Locally Recurrent or Metastatic Estrogen Receptor-Positive Breast Cancer Progressing on Treatment With a Non-Steroidal Aromatase Inhibitor (AI). Protocol", (Dec. 17, 2009), 31 pages.
Yardley, D.A., et al., "PD01-04: Entinostat, a Novel Histone Deacetylase Inhibitor, Added to Exemestane Improves PFS in Advanced Breast Cancer in a Randomized, Phase II, Double-Blind Study," Cancer Res, (2011); 71(24_Supplement):1-5.
Yardley, DA et al.; "Results of Encore 301, a Randomized, Phase II, Double-Blind, Placebo-Controlled Study of Exemestane With or Without Entinostat in Postmenopausal Women With Locally Recurrent or Metastatic Estrogen Receptor-Positive (ER+) Breast Cancer Progressing on a Nonsteroidal Aromatase Inhibitor (AI)", J. Clin. Oncol., (Sep. 2011); 29(Suppl. 27):1-19, presentation and slides.
"Syndax and merck to collaborate on immuno-oncology study evaluating entinostat in combination with keytruda in lung cancer and melanoma", 2015, 5 pages. Retrieved online: https://www.europeanpharmaceuticalreview.com/news/30492/syndax-and-merck-to-collaborate-on-immunooncology-study-evaluating-entinostat-in-combinationwith-keytmda-in-lung-cancer-and-melanoma.
Zardavas, D. et al. "Emerging Targeted Agents in Metastatic Breast Cancer"; Nat. Rev. Clin. Oncol. Advance Online Publication, (Mar. 5, 2013); 1-20.
Sundarasetty B.S. et al., "Lentivirus-induced 'Smart' dendritic cells: Pharmacodynamics and GMP-compliant production for immunotherapy against TRP2-positive melanoma" Gene Therapy (2015); 22:707-720.
Baran et al. "Important Roles for Macrophage Colony-stimulating Factor, CC Chemokine Ligand 2, and Mononuclear Phagocytes in the Pathogenesis of Pulmonary Fibrosis", Am. J. Respir. Grit. Care Med., (2007); 176:78-89.
Byrne, A.J., et al., "Pulmonary Macrophages: A New Therapeutic Pathway in Fibrosing Lung Disease?", Trends Mol Med., (2016); 22(4):303-316.

(56) References Cited

OTHER PUBLICATIONS

He, C., et al., "Accelerated development of pulmonary fibrosis via Cu, Zn-superoxide dismutase-induced alternative activation of macrophages", J Biol Chem., (2013); 288(28):20745-20757.

Pechkovsky, D.V., et al., "Alternatively activated alveolar macrophages in pulmonary fibrosis-mediator production and intracellular signal transduction," Clin Immunol., (2010); 137(1):89-101.

Raghu et al., "Treatment of Idiopathic Pulmonary Fibrosis with a New Antifibrotic Agent, Pirfenidone", Am. J. Respir. Crit. Care Med., (1999); 159:1061-1069.

Wynn, T.A., et al., "Macrophages: master regulators of inflammation and fibrosis," Semin Liver Dis., (2010); 30(3):245-257.

Chen, C. et al. "Enhancement and destruction of antibody function by somatic mutation: unequal occurrence is controlled by V gene combinatorial association," EMBO J, (1995); 14(12):2784-2794.

International Preliminary Report of International Application No. PCT/EP2014/068050, dated Mar. 1, 2016, 8 pages.

Kussie, P. H. et al. "A single engineered amino acid substitution changes antibody fine specificity," J. Immunol., (1994); 152:146-152.

Pedroza, M. et al. "Interleukin-6 Contributes to Inflammation and Remodeling in a Model of Adenosine Mediated Lung Injury," PloS One, (2011); 6(7):1-13.

Tamura, M., et al., "Structural correlates of an anticarcinoma antibody: identification of specificity-determining residues (SDRs) and development of a minimally immunogenic antibody variant by retention of SDRs only," J. Immunol., 2000, vol. 164, No. 3, pp. 1432-1441.

Garon, E., et al.; "Correlation of clinical activity of pembrolizumab (MK-3475) with immunohistochemical staining for programmed death-1 ligand (PD-L1) in ≥50% of tumor cells in a prospective non-small cell lung cancer (NSCLC) validation population," European J. Cancer (2014); 50(Suppl. 6):44-45, No. 127, 3 pages.

Twyman-Saint Victor, C., et al.; "Radiation and dual checkpoint blockade activate non-redundant immune mechanisms in cancer," Nature (2015); 520(7547):373-377.

Wedge, S.R., et al.; "AZD2171: a highly potent, orally bioavailable, vascular endothelial growth factor receptor-2 tyrosine kinase inhibitor for the treatment of cancer," Cancer Res. (2005); 65(10):4389-4400.

Xiulan et al., "119 Establishment of hybridoma clones secreting CSF-1 receptor antibodies and the biological effects of monoclonal antibodies," Journal of Cellular and Molecular Immunology, Issue 3, pp. 75-76 (1991), with English machine translation, 3 p.

* cited by examiner

— Group 1: No Treatment
— Group 2: vehicle (po, qd x 14), mIgG1 isotype control clone MOPC-21 (30 mg/kg,sc, tiwk x 2)
— Group 3: MS1 (5 mg/kg,po, qd x 14)
— Group 4: MS2 (30 mg/kg,sc, tiwk x 2)
— Group 5: MS2 (20 mg/kg,sc, biwk x 2)
— Group 6: MS1 (5 mg/kg,po, qd x 14), MS2 (30 mg/kg,sc, tiwk x 2)

MS1: entinostat
MS2: ab535

METHOD OF TREATING CANCER USING A COMBINATION OF ENTINOSTAT AND AN ANTI-CSF-1R ANTIBODY

RELATED APPLICATIONS

This application is a U.S. National Stage Application under 35 U.S.C. § 371 of International Application No. PCT/US2018/033324, filed on May 18, 2018, which claims the benefit of and priority to U.S. Provisional Application No. 62/508,842, filed May 19, 2017, the contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on May 3, 2018, is named SYND-039_001WO_327830-2173_SL.txt and is 59,194 bytes in size.

FIELD OF DISCLOSURE

This disclosure relates to therapies involving an anti-CSF-1R antibody, or anti-CSF-1 antibody, or antigen binding fragment thereof, or an inhibitor of CSF-1R activity, e.g., a small chemical entity or a small molecule CSF-1R inhibitor, in combination with an HDAC inhibitor, e.g., entinostat, and methods of treating cancer.

BACKGROUND

Increased understanding of the immune tumor microenvironment has allowed for investigation into novel immune-based biomarkers and the development of new agents that target immune pathways for therapy. The colony stimulating factor 1 (CSF-1), also known as macrophage colony stimulating factor (M-CSF) is a cytokine produced by a variety of cells, including macrophages, endothelial cells and fibroblasts. CSF-1 stimulates the survival, proliferation and function of macrophages via a specific receptor on responding cells. CSF-1 and CSF-1R expression is correlated with tumor progression and poor diagnosis in many cancer types. Tumor-associated macrophages (TAMs) can be the major component of tumour stroma and high levels of CSF-1 and CSF-1R are associated with high TAM infiltrations and poor prognosis in a number of tumour types. Therefore, an immune suppressive tumor environment mediated by CSF-1 may limit the anti-tumor activity of tumor immunotherapy and lead to low response rates.

HDAC inhibitors are a developing class of therapeutic agents that regulate hematologic and solid malignancies through chromatin remodeling and gene expression.

SUMMARY

In one aspect, this disclosure provides a method of treating cancer. The method comprises administering to a patient a combination comprising an HDAC inhibitor and a second agent selected from an anti-CSF-1R antibody or binding fragment thereof, an anti-CSF-1 antibody or antigen binding fragment thereof, and an inhibitor of CSF-1R activity.

In another aspect, this disclosure provides a kit for treating cancer. The kit comprises a combination of an HDAC inhibitor and an anti-CSF-1R antibody or anti-CSF-1 antibody or antigen binding fragment thereof or an inhibitor of CSF-1R activity. For example, the kit may also include instructions on how to use the kit.

In some embodiments, the HDAC inhibitor is entinostat.

In some embodiments, the anti-CSF-1R antibody or antigen binding fragment thereof, comprises a heavy chain, wherein the variable domain of the heavy chain comprises at least one of a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3; and/or a light chain, wherein the variable domain of the light chain comprises at least one of a CDR having the sequence given in SEQ ID NO: 1 for CDR-L1, a CDR having the sequence given in SEQ ID NO:2 for CDR-L2 and a CDR having the sequence given in SEQ ID NO: 3 for CDR-L3.

In some embodiments, the anti-CSF-1R antibody or antigen binding fragment thereof comprises a heavy chain and a light chain, wherein the variable domain of the heavy chain comprises three CDRs and the sequence of CDR-H1 has at least 60% identity or similarity to the sequence given in SEQ ID NO:4, the sequence of CDR-H2 has at least 60% identity or similarity to the sequence given in SEQ ID NO:5 and the sequence of CDR-H3 has at least 60% identity or similarity to the sequence given in SEQ ID NO:6; and wherein the variable domain of the light chain comprises three CDRs and the sequence of CDR-L1 has at least 60% identity or similarity to the sequence given in SEQ ID NO: 1, the sequence of CDR-L2 has at least 60% identity or similarity to the sequence given in SEQ ID NO:2 and the sequence of CDR-L3 has at least 60% identity or similarity to the sequence given in SEQ ID NO:3.

In some embodiments, the anti-CSF-1R antibody or antigen binding fragment thereof comprises a heavy chain, wherein the heavy chain comprises the sequence given in SEQ ID NO:23; and a light chain, wherein the light chain comprises the sequence given in SEQ ID NO:15.

In some embodiments, the anti-CSF-1R antibody or anti-CSF-1 antibody or antigen binding fragment thereof is selected from the group consisting of a complete antibody molecule having full length heavy and light chains, a Fab, modified Fab', Fab', F(ab')$_2$, Fv, VH, VL and scFv fragment thereof.

In some embodiments, the anti-CSF-1R antibody or antigen binding fragment thereof comprises a heavy chain comprising the sequence given in SEQ ID NO:27 and a light chain comprising the sequence given in SEQ ID NO:19.

In some embodiments, the anti-CSF-1R antibody or antigen binding fragment thereof cross-blocks the binding of an antibody comprising the 6 CDRs given in sequence SEQ ID NO:1 for CDR-L1, SEQ ID NO:2 for CDR-L2, SEQ ID NO:3 for CDR-L3, SEQ ID NO:4 for CDR-H1, SEQ ID NO:5 for CDR-H2 and SEQ ID NO:6 for CDR-H3.

In some embodiments, the anti-CSF-1R antibody or antigen binding fragment thereof cross-blocks the binding by binding the same epitope as the antibody which it blocks.

In some embodiments, the anti-CSF-1 antibody or antigen binding fragment thereof cross-blocks the binding by binding the same epitope as the antibody which it blocks.

In some embodiments, the anti-CSF-1R antibody or antigen binding fragment thereof comprises a binding affinity for human CSF-1R of 100 μM or less, or 10 μM or less.

In some embodiments, the anti-CSF-1 antibody or antigen binding fragment thereof comprises a binding affinity for human CSF-1 of 100 μM or less, or 10 μM or less.

In some embodiments, the cancer is characterized by overexpression of CSF-1R.

In some embodiments, the cancer is pancreatic cancer, colorectal cancer, mesothelioma, glioma, neuroblastoma, ovarian cancer, glioblastoma, myelodysplastic syndromes (MDS), breast cancer, prostate cancer, skin cancer, esophageal cancer, gastric cancer, astrocytic cancer, endometrial cancer, cervical cancer, bladder cancer, renal cancer, lung cancer, liver cancer, thyroid cancer, or head and neck cancer.

In some embodiments, the cancer is colorectal cancer and/or pancreatic cancer.

In some embodiments, the anti-CSF-1R antibody or anti-CSF-1 antibody or antigen binding fragment thereof or inhibitor of CSF-1R is administered once a week.

In some embodiments, the anti-CSF-1R antibody or anti-CSF-1 antibody or antigen binding fragment thereof or inhibitor of CSF-1R is administered once every two weeks.

In some embodiments, the anti-CSF-1R antibody or anti-CSF-1 antibody or antigen binding fragment thereof or inhibitor of CSF-1R is administered twice every week.

In some embodiments, the anti-CSF-1R antibody or anti-CSF-1 antibody or antigen binding fragment thereof or inhibitor of CSF-1R is administered three times every week.

In some embodiments, the anti-CSF-1R antibody or anti-CSF-1 antibody antigen binding fragment thereof or inhibitor of CSF-1R is administered at a dose ranging between about 0.01 mg/kg and about 1000 mg/kg (e.g., about 0.1-750 mg/kg, or about 1-100 mg/kg).

In some embodiments, the anti-CSF-1R antibody or anti-CSF-1 antibody antigen binding fragment thereof or inhibitor of CSF-1R is administered at a dose ranging between about 0.1 mg/kg and about 30 mg/kg.

In some embodiments, the anti-CSF-1R antibody or anti-CSF-1 antibody antigen binding fragment thereof or inhibitor of CSF-1R activity is administered at a dose ranging between about 0.1 mg/kg and about 10 mg/kg.

In some embodiments, the anti-CSF-1R antibody or anti-CSF-1 antibody or antigen binding fragment thereof or inhibitor of CSF-1R activity is administered at a dose of about 0.1 mg/kg, 0.5 mg/kg, 1 mg/kg, 1.5 mg/kg, 3 mg/kg, 5 mg/kg, 6 mg/kg, 7.5 mg/kg, or about 10 mg/kg.

In some embodiments, the inhibitor of CSF-1R activity is a small chemical entity or a small molecule CSF-1R inhibitor. For example, the small chemical entity or small molecule CSF-1R inhibitor has a molecular weight of not greater than 5 kDa, e.g., ≤ about 4 kDa, ≤ about 3 kDa, ≤ about 1.5 kDa or ≤ about 1 kDa.

In some embodiments, entinostat is administered orally.

In some embodiments, entinostat is administered once weekly or twice weekly.

In some embodiments, entinostat is administered weekly. In some embodiments, entinostat is administered every two weeks.

In some embodiments, entinostat is administered once every week at a dose of 3 mg.

In some embodiments, entinostat is administered once every week at a dose of 5 mg.

In some embodiments, entinostat is administered once every two weeks at a dose of 10 mg.

In some embodiments, entinostat is administered first.

In some embodiments, entinostat and the second agent (e.g., anti-CSF-1R antibody or anti-CSF-1 antibody or antigen binding fragment thereof, or an inhibitor of CSF-1R activity) are administered simultaneously.

In some embodiments, the HDAC inhibitor (e.g., entinostat) and the second agent (e.g., an anti-CSF-1R antibody or antigen binding fragment thereof, an anti-CSF-1 antibody or antigen binding fragment thereof, or an inhibitor of CSF-1R activity) are administered in temporal proximity, e.g., in temporal proximity for treating cancer.

In some embodiments, the disclosure provides a synergistic composition of an HDAC inhibitor (e.g., entinostat) and a second agent (e.g., an anti-CSF-1R antibody or antigen binding fragment thereof, an anti-CSF-1 antibody or antigen binding fragment thereof, or an inhibitor of CSF-1R activity), wherein the HDAC inhibitor and the second agent come into contact with each other in the human body (e.g., only in the human body).

In some embodiments, the disclosure provides a method of preparing a composition by bringing an HDAC inhibitor (e.g., entinostat) and a second agent (e.g., an anti-CSF-1R antibody or antigen binding fragment thereof, an anti-CSF-1 antibody or antigen binding fragment thereof, or an inhibitor of CSF-1R activity) into contact with each other at a locus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
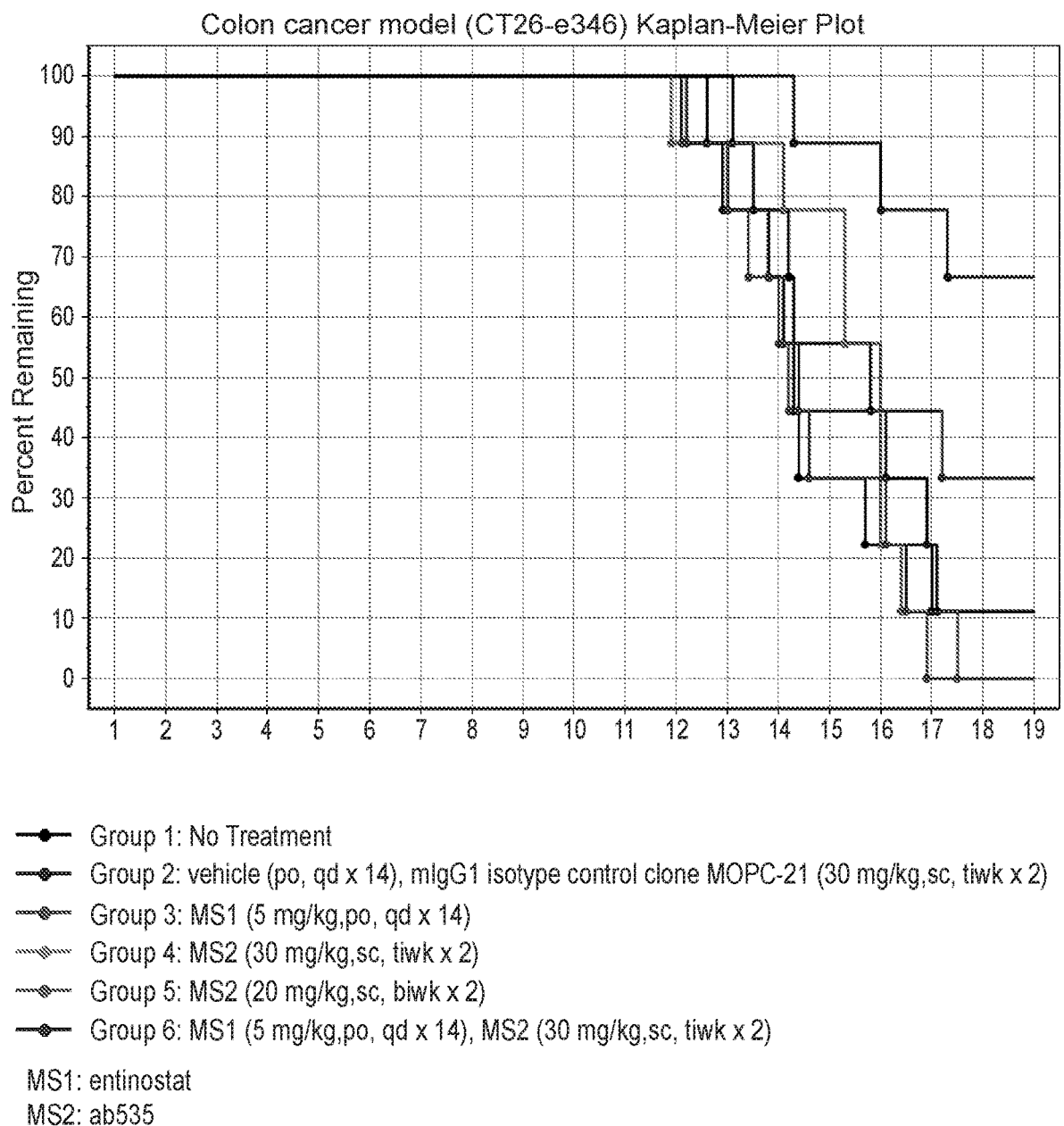
FIG. 1 is a survival plot showing that the combination of entinostat and Ab535 therapy improves animal survival.

The present disclosure is based at least in part upon the conception that, anti-CSF-1R antibody or anti-CSF-1 antibody or antigen binding fragment thereof or an inhibitor of CSF-1R activity and an HDAC inhibitor can be used in a combination to treat tumors with superior results (e.g., reduced Tumor Infiltrating Lymphocytes (TIL) or adverse effects) than those achieved with the anti-CSF-1R antibody or anti-CSF-1 antibody or antigen binding fragment thereof or an inhibitor of CSF-1R activity alone or the HDAC inhibitor alone. The methods may further include treatments wherein the combination is supplemented with one or more therapeutic agents or therapies.

In one aspect, the present disclosure provides a combination comprising an anti-CSF-1R antibody or anti-CSF-1 antibody or antigen binding fragment thereof an inhibitor of CSF-1R activity and an HDAC inhibitor, and a method of using the combination to treat diseases, such as those the cause of which can be influenced by modulating immune cell profiling of Tumor infiltrating lymphocytes (TIL) and/or other proteins, e.g., cancer. In some embodiments, the present disclosure features a combination comprising an anti-CSF-1R antibody or anti-CSF-1 antibody or antigen binding fragment thereof or an inhibitor of CSF-1R activity and an HDAC inhibitor including benzamides (e.g., entinostat).

The method comprises administering to a subject in need thereof an effective amount of an anti-CSF-1R antibody or anti-CSF-1 antibody or antigen binding fragment thereof or an inhibitor of CSF-1R activity and an HDAC inhibitor, e.g., by inhibiting tumor growth, reducing Tumor Associated Macrophages (TAMs) and intra-tumor T regulatory cell population and/or increasing CD8/T-regulatory cell ratio in tumors.

The kits, combinations and methods disclosed herein are suitable for treating cancer or inhibiting cancer cell proliferation, such as a adenocarcinoma, e.g., colorectal cancer and/or pancreatic cancer.

The present disclosure further provides uses of any compositions or combinations described herein in the manufacture of medicament for treating a disease. Such diseases include, for example, cancer, a precancerous condition, or a disease influenced by modulating the immune cell profiling of Tumor infiltrating lymphocytes (TIL) or other proteins.

The present disclosure provides use in a combinational therapy, wherein the compound comprises an anti-CSF-1R antibody or anti-CSF-1 antibody or antigen binding fragment thereof or an inhibitor of CSF-1R activity and an HDAC inhibitor (e.g., entinostat).

Colony stimulating factor-1 (CSF-1) is a cytokine frequently produced by several cancers, including melanoma. The secreted CSF-1 binds to the tyrosine kinase receptor CSF-1R on the myeloid cells, which results in increased proliferation and differentiation of myeloid cells into type M2 macrophages and myeloid derived suppressor cells (MDSC), and their recruitment into tumors. (Mok et al., Mol Cancer Res 2014 74(1): 153-161). Established solid tumors consist of both transformed neoplastic cells and non-transformed host cells such as stromal cells, lymphocytes, dendritic cells, macrophages, and MDSC. In order to escape immune responses, tumor cells manipulate the surrounding tumor microenvironment by producing cytokines that suppress cytolytic T-cells and recruit immune suppressive cells. (Mok et al.). Consequently, an immune suppressive tumor environment mediated by CSF-1 may limit the anti-tumor activity of tumor immunotherapy and lead to low response rates.

Histone deacetylase (HDAC) inhibitors have been shown to effect human monocyte responses to the colony-stimulating factors CSF-1 and CSF-2. Reports indicate a first-in-class selective class IIa histone deacetylase (HDAC) inhibitor, TMP195, influenced human monocyte responses to the colony-stimulating factors CSF-1 and CSF-2 in vitro and that class IIa HDAC inhibition reduced breast tumors and metastases through anti-tumor macrophages (Guerriero et al., Nature, 2017 543, 428-432).

Anti-CSF-1R Antibody

The CSF-1 receptor (CSF-1R) is also referred to as the c-fms gene product or CD115. CSF-1R is a 165 kDa type 1 TM glycoprotein belonging to the type III receptor tyrosine kinase family. In addition to CSF-1, the structurally similar but sequence unrelated molecule IL-34 has also been shown to be a ligand for CSF-1R (Lin, et al., 2008, Science 320:807-811). Expression of CSF-1R is restricted to cells of the monocyte-macrophage lineage, both circulating and resident tissue populations, and osteoclasts. In addition, it is expressed in a number of cells of the female reproductive system including oocytes, decidual cells and trophoblasts.

Binding of the ligand CSF-1 to the CSF-1 receptor results in the phosphorylation of the receptor on one or more tyrosine residues, through the action of the tyrosine kinase domain. This phosphorylation can be detected because antibodies are available that bind to the receptor only after phosphorylation (for example Phospho-M-CSF-Receptor (Tyr546) antibody #3083 from Cell Signaling Technology).

Expression of CSF-1 and CSF-1R correlates with tumor progression and poor diagnosis in many cancer types. Tumor-associated macrophages (TAMs) can be the major component of tumor stroma and high levels of CSF-1 and CSF-1R are associated with high TAM infiltrations and poor prognosis in a number of tumor types. High expression of Tumor Infiltrating Lymphocytes (TIL) on tumor cells has been found to correlate with poor prognosis and survival in various other solid tumor types. There is a need to provide new anti-CSF-1R antibodies suitable for therapeutic applications. Without being bound by any theory it is contemplated that the CSF-1/CSF-1R pathway plays a critical role in the tumor immune evasion and could be considered an attractive target for therapeutic intervention in several solid organ types.

Antibodies to CSF-1R are known in the art. Sherr, C. J. et al., 1989, Blood 73:1786-1793 describes antibodies against CSF-1R that inhibit the CSF-1 activity (Sherr, C. J. et al., 1989, Blood 73:1786-1793). WO2009/026303 discloses anti-CSF-1R antibodies which bind to human CSF-1R and in vivo mouse tumor models using an anti-murine CSF-1R antibody. WO2011/123381 discloses anti-CSF-1R antibodies which internalize CSF-1R and have ADCC activity. WO2011/123381 also discloses in vivo mouse tumor models using an anti-murine CSF-1R antibody. WO2011/140249 discloses anti-CSF-1R antibodies which block binding of CSF-1 to CSF-1R and are stated to be useful in the treatment of cancer. WO2009/112245 discloses an anti-CSF-1R IgG1 antibody which inhibits CSF-1 binding to CSF-1R and is stated to be useful in the treatment of cancer, inflammatory bowel disease and rheumatoid arthritis. WO2011/131407 discloses an anti-CSF-1R antibody which inhibits CSF-1 binding to CSF-1R and is stated to be useful in the treatment of bone loss and cancer. WO2011/107553 discloses an anti-CSF-1R antibody which inhibits CSF-1 binding to CSF-1R thought to be useful in the treatment of bone loss and cancer. WO2011/070024 discloses anti-CSF-1R antibodies which bind to human CSF-1R fragment delD4.

In some embodiments, the antibodies provided by the present disclosure are capable of blocking ligand binding to CSF-1R. Blocking as employed herein refers to physically blocking such as occluding the receptor but will also include where the antibody or fragments binds an epitope that causes, for example a conformational change which means that the natural ligand to the receptor no longer binds (referred to herein as allosteric blocking or allosteric inhibition). In one embodiment, the antibodies of the present disclosure bind all isotypes of CSF-1R, for example those with variations in the ECD domain, such as V23G, A245S, H247P, V279M and combinations of two, three or four of said variations.

CSF-1 and IL-34 are both ligands for CSF-1R and the antibodies of the disclosure preferably inhibit the activity both CSF-1 and IL-34 in a functional cellular screen. The antibodies according to the present disclosure also preferably do not cause CSF-1R activation and/or CSF-1R internalization. The antibodies according to the present disclosure also preferably selectively deplete the non-classical population of monocytes in vivo.

Non-classic monocytes generally refer to monocytes with low expression of CD14 and high expression of CD16. This population of monocytes are thought to be pre-cursors of tumor associated macrophages.

The antibody molecules of the present disclosure suitably have a high binding affinity. Affinity may be measured using any suitable method known in the art, including techniques such as surface plasmon resonance, for example BIAcore, as described in the Examples herein, using isolated natural or recombinant CSF-1R or a suitable fusion protein/polypeptide. In one example affinity is measured using recombinant human CSF-1R extracellular domain as described in the Examples herein. In one example the recombinant human CSF-1R extracellular domain used is a monomer. Suitably the antibody molecules of the present disclosure have a binding affinity for isolated human CSF-1R of about 1 nM or less than 1 nM. In one embodiment the antibody molecule of the present disclosure has a binding affinity of about 500 μM or lower. In one embodiment the antibody molecule of the present disclosure has a binding affinity of about 250 μM or lower. In one embodiment the antibody molecule of the present disclosure has a binding affinity of about 200 μM or lower. In one embodiment the present disclosure provides an anti-CSF-1R antibody with a binding affinity of about 100 μM or lower. In one embodiment the present disclosure provides a humanized anti-CSF-1R antibody with a binding affinity of about 100 μM or lower, preferably about 10 μM or lower, more preferably about 5 μM or lower. In some embodiment the present disclosure provides a humanized anti-CSF-1R antibody with a binding affinity of about 100 μM or lower, preferably about 10 μM or lower, more preferably about 5 μM or lower The lower the numerical value of the affinity the higher the affinity of the antibody or fragment for the antigen.

Human CSF-1R as employed herein refers to the human protein name CSF-1R or a biological active fragment thereof.

The present disclosure provides anti-CSF-1R antibodies, including humanized antibodies. The antibodies were generated from immunization of rats with rat fibroblasts that were transfected with a vector expressing CSF-1R extracellular domain.

The present disclosure provides an antibody comprising a heavy chain and/or a light chain, wherein the heavy chain and/or light chain comprise at least one CDR derived from the anti-CSF-1R antibody 969.2.

Ab969.2 is a full-length humanized IgG4 molecule; the light chain comprises a human kappa chain constant region (Km3 allotype) and the heavy chain comprises a human gamma-4 heavy chain constant region with the hinge stabilizing mutation S241P (Angal et al., 1993). A potential DG isomerization motif is present within the light chain variable region at the junction of CDR-L2 and the framework. The sequences of Ab969.2 full antibody heavy and light chains are shown in SEQ ID NOs: 27 and 19.

The residues in antibody variable domains are conventionally numbered according to a system devised by Kabat et al., 1987. This system is set forth in Kabat et al., 1987, in Sequences of Proteins of Immunological Interest, U.S. Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M., J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

Antibodies for use in the present disclosure may be obtained using any suitable method known in the art. The CSF-1R polypeptide/protein including fusion proteins, cells (recombinantly or naturally) expressing the polypeptide can be used to produce antibodies which specifically recognize CSF-1R. The polypeptide may be the 'mature' polypeptide or a biologically active fragment or derivative thereof. The human protein is registered in UniProt under the number P07333.

Antibodies generated against the CSF-1R polypeptide may be obtained, where immunization of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Screening for antibodies can be performed using assays to measure binding to human CSF-1R and/or assays to measure the ability to block ligand binding to the receptor. Examples of suitable assays are described in the Examples herein.

In some embodiments, the antibody is an anti-CSF-1R antibody or binding fragment thereof comprising a heavy chain, wherein the variable domain of the heavy chain comprises at least one of a CDR having the sequence given in SEQ ID NO: 4 for CDR-H1, a CDR having the sequence given in SEQ ID NO:5 for CDR-H2 and a CDR having the sequence given in SEQ ID NO:6 for CDR-H3. Preferably the variable domain of the heavy chain comprises the sequence given in SEQ ID NO: 4 for CDR-H1, the sequence given in SEQ ID NO:5 for CDR-H2 and the sequence given in SEQ ID NO:6 for CDR-H3.

In some embodiments, the antibody of the disclosure is an anti-CSF-1R antibody or binding fragment thereof comprising a heavy chain as defined above and additionally comprising a light chain wherein the variable domain of the light chain comprises at least one of a CDR having the sequence given in SEQ ID NO: 1 for CDR-L1, a CDR having the sequence given in SEQ ID NO:2 for CDR-L2 and a CDR having the sequence given in SEQ ID NO:3 for CDR-L3. The variable domain of the light chain preferably comprises the sequence given in SEQ ID NO:1 for CDR-L1, the sequence given in SEQ ID NO:2 for CDR-L2 and the sequence given in SEQ ID NO:3 for CDR-L3.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., 1985, Monoclonal Antibodies and Cancer Therapy, pp 77-96, Alan R Liss, Inc.).

In one embodiment, at least one amino acid is replaced with a conservative substitution in one or more CDRs selected from the group consisting independently of: any one of CDR-H1, CDR-H2, CDR-H3, CDR-L1, CDR-L2, CDR-L3; any one of the combinations CDR-H1 and H2, CDR-H1 and H3, CDR-H1 and L1, CDR-H1 and L2, CDR-H1 and L3, CDR-H2 and H3, CDR-H2 and L1, CDR-H2 and L2, CDR-H2 and L3, CDR-H3 and L1, CDR-H3 and L2, CDR-H3 and L3, CDR-L1 and L2, CDR-L1 and L3, CDR-L2 and L3; CDR-H1, H2 and H3, CDR-H1, H2 and L1, CDR-H1, H2 and L2, CDR-H1, H2 and L3, CDR-H2, H3 and L1, CDR-H2, H3 and L2, CDR-H2, H3 and L3, CDR-H3, L1 and L2, CDR-H3, L1 and L3, CDR-L1, L2, L3; any one of the combinations CDR-H1, H2, H3 and L1, CDR-H1, H2, H3 and L2, CDR-H1, H2, H3 and L3, CDR-H2, H3, L1 and L2, CDR-H2, H3, L2 and L3, CDR-H3, L1, L2 and L3, CDR-L1, L2, L3 and H1, CDR-L1, L2, L3 and H2, CDR-L1, L2, L3 and H3, CDR-L2, L3, H1 and H2, CDR-H1, H2, H3, L1 and L2, CDR-H1, H2, H3, L1 and L3, CDR-H1, H2, H3, L2 and L3, CDR-L1, L2, L3, H1 and H2, CDR-L1, L2, L3, H1 and H3, CDR-L1, L2, L3, H2 and H3; and the combination CDR-H1, H2, H3, L1, L2 and L3.

In some embodiments, there is provided an anti-CSF-1R antibody or binding fragment thereof, wherein the variable domain of the heavy chain comprises three CDRs and the sequence of CDR-H1 has at least 60%, 70%, 80%, 90% or 95% identity or similarity to the sequence given in SEQ ID NO:4, the sequence of CDR-H2 has at least 60%, 70%, 80%, 90% or 95% identity or similarity to the sequence given in SEQ ID NO:5 and the sequence of CDR-H-3 has at least 60%, 70%, 80%, 90% or 95% identity or similarity to the sequence given in SEQ ID NO:6. Preferably, the anti-CSF-1R antibody or binding fragment thereof, additionally comprising a light chain, wherein the variable domain of the light chain comprises three CDRs and the sequence of CDR-L1 has at least 60%, 70%, 80%, 90% or 95% identity or similarity to the sequence given in SEQ ID NO:1, the sequence of CDR-L2 has at least 60%, 70%, 80%, 90% or 95% identity or similarity to the sequence given in SEQ ID NO:2 and the sequence of CDR-L3 has at least 60% identity or similarity to the sequence given in SEQ ID NO:3.

In some embodiments, the anti-CSF-1R antibody or antigen binding fragment thereof cross-blocks the binding of an antibody comprising the 6 CDRs given in sequence SEQ ID NO:1 for CDR-L1, SEQ ID NO:2 for CDR-L2, SEQ ID NO:3 for CDR-L3, SEQ ID NO:4 for CDR-H1, SEQ ID NO:5 for CDR-H2 and SEQ ID NO:6 for CDR-H3, for example with affinity of 100 µM or less, in particular wherein the cross blocking is allosteric. In some embodiments, the anti-CSF-1R-antibody or binding fragment thereof inhibits or overlaps with the binding of CSF-1 and/or IL-34 to the extracellular domain of the CSF-1R receptor.

In one embodiment there is provided an anti-CSF-1R antibody or antigen binding fragment thereof which cross-blocks the binding of an antibody comprising a the 6 CDRs given in sequence SEQ ID NO:1 for CDR-L1, SEQ ID NO:2 for CDR-L2, SEQ ID NO:3 for CDR-L3, SEQ ID NO:4 for CDR-H1, SEQ ID NO:5 for CDR-H2 and SEQ ID NO:6 for CDR-H3, for example with affinity of 100 µM or less, in particular wherein the antibody cross-blocks the binding by binding the same epitope as the antibody which it blocks.

In some embodiments, the antibody has a heavy chain comprising the sequence given in SEQ ID NO: 27 and a light chain comprising the sequence given in SEQ ID NO: 19. Also provided is an anti-CSF-1R antibody or binding fragment thereof, in which the heavy and light chains are at least 80% (preferably 85%, 90%, 95% or 98%) identical or similar to a heavy chain comprising the sequence given in SEQ ID NO: 27 and a light chain comprising the sequence given in SEQ ID NO: 19. In one embodiment, the light chain has or consists of the sequence given in SEQ ID NO: 19 and the heavy chain has or consists of the sequence given in SEQ ID NO: 27. In another embodiment, the light chain has or consists of the sequence of SEQ ID NO: 19 and the heavy chain has or consists of the sequence of SEQ ID NO: 27, wherein the amino acid lysine at position 453 of SEQ ID NO: 27 is missing or deleted.

Also provided by the present disclosure is a specific region or epitope of human CSF-1R which is bound by an antibody of the disclosure, in particular an antibody 969.g2 comprising the heavy chain sequence gH2 (SEQ ID NO: 27) and/or the light chain sequence gL7 (SEQ ID NO: 19).

This specific region or epitope of the human CSF-1R polypeptide can be identified by any suitable epitope mapping method known in the art in combination with any one of the antibodies provided by the present disclosure. Examples of such methods include screening peptides of varying lengths derived from CSF-1R for binding to the antibody of the present disclosure with the smallest fragment that can specifically bind to the antibody containing the sequence of the epitope recognized by the antibody (for example a peptide in the region of about 5 to 20, preferably about 7 amino acids in length). The CSF-1R peptides may be produced synthetically or by proteolytic digestion of the CSF-1R polypeptide. Peptides that bind the antibody can be identified by, for example, mass spectrometric analysis. In another example, NMR spectroscopy or X-ray crystallography can be used to identify the epitope bound by an antibody of the present disclosure. Once identified, the epitopic fragment, which binds an antibody of the present disclosure, can be used, if required, as an immunogen to obtain additional antibodies, which bind the same epitope.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the CSF-1R antibody and fragments of the disclosure may be engineered to have an appropriate isoelectric point. This may lead to antibodies and/or fragments with more robust properties, in particular suitable solubility and/or stability profiles and/or improved purification characteristics.

In some embodiments, the disclosure provides a humanized CSF-1R antibody engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY available on the the Internet at expasy.ch/tools/pi_tool.html, and _ut-arles.up.univmrs.fr/w3bb/d_abim/compo-p.html, may be used to predict the isoelectric point of the antibody or fragment. It will be appreciated that the affinity of antibodies disclosed herein may be altered using any suitable method known in the art. The present disclosure therefore also relates to variants of the antibody molecules of the present disclosure, which have an improved affinity for CSF-1R. Such variants can be obtained by a number of affinity maturation protocols including mutating the CDRs (Yang et al., 1995, J. Mol. Biol., 254:392-403), chain shuffling (Marks et al., 1992, Bio/Technology, 10:779-783), use of mutator strains of *E. coli* (Low et al., 1996, J. Mol. Biol., 250:359-368), DNA shuffling (Patten et al., 1997, Curr. Opin. Biotechnol., 8:724-733), phage display (Thompson et al., J. Mol. Biol., 256, 77-88, 1996) and sexual PCR (Crameri et al., 1998, Nature, 391:288-291). Vaughan et al. (supra) discusses these methods of affinity maturation.

As used herein a "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the disclosure include humanized and/or chimeric monoclonal antibodies.

The antibody of the present disclosure may be conjugated to one or more effector molecule(s). It will be appreciated that the effector molecule may comprise a single effector molecule or two or more such molecules so linked as to form a single moiety that can be attached to the antibodies of the present disclosure. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO93/06231, WO92/22583, WO89/00195, WO89/01476 and WO03/031581. Alternatively, where the effector molecule is a protein or polypeptide the linkage may be achieved using recombinant DNA procedures, for example as described in WO86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups, such as fluorescent compounds or compounds which may be detected by NMR or ESR spectroscopy.

Effector molecules also include, but are not limited to, antimetabolites (e.g. methotrexate, 6-mercaptopurine, 6-thioguanine, cytarabine, 5-fluorouracil, dacarbazine), alkylating agents (e.g. mechlorethamine, thiotepa, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), nerve growth factor (NGF) or other growth factor and immunoglobulins.

The effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, and albumin binding proteins or albumin binding compounds such as those described in WO05/117984. In some embodiments, the half-life provided by an effector molecule, which is independent of CSF-1R, is advantageous.

In some embodiments, there is provided a purified anti-CSF-1R antibody or fragment, for example a humanized antibody or fragment, in particular an antibody or fragment disclosed herein, in substantially purified from, in particular free or substantially free of endotoxin and/or host cell protein or DNA. Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 350 μg per mg or less, 300 μg per mg or less, 250 μg per mg or less, 200 μg per mg or less, 150 μg per mg or less, 100 μg per mg or less, 50 μg per mg or less, 40 μg per mg or less, in particular 20 μg per mg or less, as appropriate.

Other examples of anti-CSF-1R antibodies and effector molecules are described in WO 2015/028455, the contents of which are hereby incorporated by reference in its entirety.

Nucleic Acids, Polypeptides

CDR-L1: LASEDIYDNLA (SEQ ID NO: 1)

CDRL2: YASSLQD (SEQ ID NO: 2)

CDR-L3: LQDSEYPWT (SEQ ID NO: 3)

CDR-H1: GFSLTTYGMGVG (SEQ ID NO: 4)

CDR-H2: NIWWDDDKYYNPSLKN (SEQ ID NO: 5)

CDR-H3: IGPIKYPTAPYRYFDF (SEQ ID NO: 6)

Rat Ab 969 VL region: DIQMTQSPAS LSASLGETVS IECLASEDIY
DNLAWYQKKP GKSPHLLIYY ASSLQDGVPS RFSGSGSGTQ YSLKINSLES
EDAATYFCLQ DSEYPWTFGG GTKLELK (SEQ ID NO: 7)

Rat Ab 969 VL region: gacatccaga tgacacagtc tccagcttcc ctgtctgcat ctctgggaga
aactgtctcc atcgaatgtc tagcaagtga ggacatttac gataatttag cgtggtacca gaagaagcca ggaaaatctc
ctcacctcct catctattat gcaagtagct tgcaagatgg ggtcccatca cggttcagtg gcagtggatc tggcacacag
tattctctca aaatcaacag cctggaatct gaagatgctg cgacttattt ctgtctacag gattctgagt atccgtggac
gttcggtgga ggcaccaagc tggaattgaa a (SEQ ID NO: 8)

Rat Ab 969 VL region with signal sequence underlined and italicized: *MGVPTQLLVL*
*LLLWITDAIC* DIQMTQSPAS LSASLGETVS IECLASEDIY DNLAWYQKKP
GKSPHLLIYY ASSLQDGVPS RFSGSGSGTQ YSLKINSLES EDAATYFCLQ
DSEYPWTFGG GTKLELK (SEQ ID NO: 9)

Rat Ab 969 VL region with signal sequence underlined and italicized: *atgggtgtcc*
*ccactcagct cttggtgttg ttgctgctgt ggattacaga tgccatatgt* gacatccaga tgacacagtc tccagcttcc
ctgtctgcat ctctgggaga aactgtctcc atcgaatgtc tagcaagtga ggacatttac gataatttag cgtggtacca
gaagaagcca ggaaaatctc ctcacctcct catctattat gcaagtagct tgcaagatgg ggtcccatca cggttcagtg
gcagtggatc tggcacacag tattctctca aaatcaacag cctggaatct gaagatgctg cgacttattt ctgtctacag
gattctgagt atccgtggac gttcggtgga ggcaccaagc tggaattgaa a (SEQ ID NO: 10)

Rat Ab 969 VH region: QVTLKESGPG ILQPSQTLSL TCTFSGFSLT
TYGMGVGWIR QPSGKGLEWLANIWWDDDKY YNPSLKNRLT ISKDTSNNQA
FLKLTNVHTS DSATYYCARIGPIKYPTAPY RYFDFWGPGT MVTVS (SEQ ID NO: 11)

Rat Ab 969 VH region: caggttactc tgaaagagtc tggccctggg atattgcagc cctcccagac
cctcagtctg acttgcactt tctctggggtt ttcactgacc acttatggta tgggtgtggg ctggattcgt cagccttcag
ggaagggtct ggagtggctg caaacatttt ggtgggatga tgataagtat tacaatccat ctctgaaaaa ccggctcaca
atctccaagg acacctccaa caaccaagca ttcctcaagc tcaccaatgt acacacttca gattctgcca catactactg
tgctcggata gggccgatta ataccccgac ggcccctac cggtactttg acttctgggg cccaggaacc atggtcaccg tctcg
(SEQ ID NO: 12)

Rat Ab 969 VH region with signal sequence underlined and italicized: *MDRLTSSFLL*
*LIVPAYVLSQ* VTLKESGPGI LQPSQTLSLT CTFSGFSLTT YGMGVGWIRQ
PSGKGLEWLA NIWWDDDKYY NPSLKNRLTI SKDTSNNQAF LKLTNVHTSD
SATYYCARIG PIKYPTAPYR YFDFWGPGTM VTVS (SEQ ID NO: 13)

Rat Ab 969 VH region with signal sequence underlined and italicized: *atggacaggc*
*ttacttcctc attcctactg ctgattgtcc ctgcatatgt cctgtct*cag gttactctga aagagtctgg ccctgggata ttgcagccct
cccagaccct cagtctgact tgcactttct ctgggTTTTc actgaccact atggtatggg tgtgggctg gattcgtcag
ccttcaggga agggtctgga gtggctgca aacatttggt gggatgatga taagtattac aatccatctc tgaaaaaccg
gctcacaatc tccaaggaca cctccaacaa ccaagcattc ctcaagctca ccaatgtaca cacttcagat tctgccacat
actactgtgc tcggataggg ccgattaaat acccgacggc cccctaccgg tactttgact tctggggccc aggaaccatg
gtcaccgtct cg (SEQ ID NO: 14)

969 gL7 V-region: DIQMTQSPSS LSASVGDRVT ITCLASEDIY DNLAWYQQKP
GKAPKLLIYY ASSLQDGVPS RFSGSGSGTD YTLTISSLQP EDFATYYCLQ
DSEYPWTFGG GTKVEIK (SEQ ID NO: 15)

969 gL7 V-region: gacatacaga tgactcagtc accctcaagc ctgagtgcca gtgtgggaga cagggtgaca
atcacctgtc tggcctccga ggatatctac gataacctgg catggtatca gcagaaacct ggaaaggctc caagctcct
gatttattat gcctcctctc tccaagacgg cgttccatct cggttcagcg gaagcggctc cgggacggat tacacactga
caattagctc tctgcaaccg gaggattllg ctacttacta ctgcctgcaa gactccgaat acccatggac cttcggtggt
ggcaccaaag tggaaatcaa g (SEQ ID NO: 16)

969 gL7 V-region with signal sequence underlined and italicized: *MSVPTQVLGL*
*LLLWLTDARC* DIQMTQSPSS LSASVGDRVT ITCLASEDIY DNLAWYQQKP
GKAPKLLIYY ASSLQDGVPS RFSGSGSGTD YTLTISSLQP EDFATYYCLQ
DSEYPWTFGG GTKVEIK (SEQ ID NO: 17)

969 gL7 V-region with signal sequence underlined and italicized: *atgagcgtgc*
*ctactcaagt cttggggctg ctcttgcttt ggcttaccga cgcaagatgc* gacatacaga tgactcagtc accctcaagc
ctgagtgcca gtgtgggaga cagggtgaca atcacctgtc tggcctccga ggatatctac gataacctgg catggtatca
gcagaaacct ggaaaggctc caagctcct gatttattat gcctcctctc tccaagacgg cgttccatct cggttcagcg
gaagcggctc cgggacggat tacacactga caattagctc tctgcaaccg gaggattttg ctacttacta ctgcctgcaa
gactccgaat acccatggac cttcggtggt ggcaccaaag tggaaatcaa g (SEQ ID NO: 18)

969 gL7 light chain (V + constant): DIQMTQSPSS LSASVGDRVT ITCLASEDIY
DNLAWYQQKP GKAPKLLIYY ASSLQDGVPS RFSGSGSGTD YTLTISSLQP
EDFATYYCLQ DSEYPWTFGG GTKVEIKRTV AAPSVFIFPP SDEQLKSGTA

| Nucleic Acids, Polypeptides |
| --- |
| SVVCLLNNFY PREAKVQWKV DNALQSGNSQ ESVTEQDSKD STYSLSSTLT<br>LSKADYEKHK VYACEVTHQG LSSPVTKSFN RGEC (SEQ ID NO: 19)<br><br>969 gL7 light chain (V + constant): gacatacaga tgactcagtc accctcaagc ctgagtgcca<br>gtgtgggaga cagggtgaca atcacctgtc tggcctccga ggatatctac gataacctgg catggtatca gcagaaacct<br>ggaaaggctc ccaagctcct gatttattat gcctcctctc tccaagacgg cgttccatct cggttcagcg gaagcggctc<br>cgggacggat tacacactga caattagctc tctgcaaccg gaggattttg ctacttacta ctgcctgcaa gactccgaat<br>acccatggac cttcggtggt ggcaccaaag tggaaatcaa gcgtacggta gcggccccat ctgtcttcat cttcccgcca<br>tctgatgagc agttgaaatc tggaactgcc tctgttgtgt gcctgctgaa taacttctat cccagagagg ccaaagtaca<br>gtggaaggtg gataacgccc tccaatcggg taactcccag gagagtgtca cagagcagga cagcaaggac agcacctaca<br>gcctcagcag caccctgacg ctgagcaaag cagactacga gaaacacaaa gtctacgcct gcgaagtcac ccatcagggc<br>ctgagctcgc cgtcacaaa gagcttcaac aggggagagt gt (SEQ ID NO: 20)<br><br>969 gL7 light chain (V + constant) with signal sequence underlined and italicized:<br>*MSVPTQVLGL LLLWLTDARC* DIQMTQSPSS LSASVGDRVT ITCLASEDIY<br>DNLAWYQQKP GKAPKLLIYY ASSLQDGVPS RFSGSGSGTD YTLTISSLQP<br>EDFATYYCLQ DSEYPWTFGG GTKVEIKRTV AAPSVFIFPP SDEQLKSGTA<br>SVVCLLNNFY PREAKVQWKV DNALQSGNSQ ESVTEQDSKD STYSLSSTLT<br>LSKADYEKHK VYACEVTHQG LSSPVTKSFN RGEC (SEQ ID NO: 21)<br><br>969 gL7 light chain (V + constant) with signal sequence underlined and italicized:<br>*atgagcgtgc ctactcaagt cttggggctg ctcttgcttt ggcttaccga cgcaagatgc* gacatacaga tgactcagtc<br>accctcaagc ctgagtgcca gtgtgggaga cagggtgaca atcacctgtc tggcctccga ggatatctac gataacctgg<br>catggtatca gcagaaacct ggaaaggctc ccaagctcct gatttattat gcctcctctc tccaagacgg cgttccatct<br>cggttcagcg gaagcggctc cgggacggat tacacactga caattagctc tctgcaaccg gaggattttg ctacttacta<br>ctgcctgcaa gactccgaat acccatggac cttcggtggt ggcaccaaag tggaaatcaa gcgtacggta gcggccccat<br>ctgtcttcat cttcccgcca tctgatgagc agttgaaatc tggaactgcc tctgttgtgt gcctgctgaa taacttctat<br>cccagagagg ccaaagtaca gtggaaggtg gataacgccc tccaatcggg taactcccag gagagtgtca cagagcagga<br>cagcaaggac agcacctaca gcctcagcag caccctgacg ctgagcaaag cagactacga gaaacacaaa gtctacgcct<br>gcgaagtcac ccatcagggc ctgagctcgc cgtcacaaa gagcttcaac aggggagagtgt (SEQ ID NO: 22)<br><br>969 gH2 V-region: EVTLKESGPA LVKPTQTLTL TCTFSGFSLT TYGMGVGWIR<br>QPPGKALEWL ANIWWDDDKY YNPSLKNRLT ISKDTSKNQV VLTMTNMDPV<br>DTATYYCARI GPIKYPTAPY RYFDFWGQGT MVTVS (SEQ ID NO: 23)<br><br>969 gH2 V-region: gaagtgacac tcaaggagtc tggacccgct ctggtgaaac caacccaaac actcactttg<br>acatgtactt ttagtggctt ctcattgact acctatggaa tgggcgtggg atggatcaga cagccacctg gcaaggctct<br>ggaatggctg gccaacatct ggtgggatga cgacaagtac tataaccgt ccctgaaaaa ccggctgacc attagcaagg<br>atacttctaa aaatcaagtg gtgctgacca tgacaaatat ggatcccgtt gacaccgcaa cctactactg cgcccgcatt<br>ggtcccataa agtaccctac ggcaccttac cgatatttcg acttttgggg ccaagggaca atggttactg tctcg (SEQ ID NO: 24)<br><br>969 gH2 V-region with signal sequence underlined and italicized: *MEWSWVFLFF<br>LSVTTGVHSE* VTLKESGPAL VKPTQTLTLT CTFSGFSLTT YGMGVGWIRQ<br>PPGKALEWLA NIWWDDDKYY NPSLKNRLTI SKDTSKNQVV LTMTNMDPVD<br>TATYYCARIG PIKYPTAPYR YFDFWGQGTM VTVS (SEQ ID NO: 25)<br><br>969 gH2 V-region with signal sequence underlined and italicized: *atggagtggt<br>cctgggtgtt tctgttcttc ctgagtgtga ccaccggggt ccactccgga* gtgacactca aggagtctgg acccgctctg<br>gtgaaaccaa cccaaacact cactttgaca tgtacttta gtggcttctc attgactacc tatggaatgg gcgtgggatg<br>gatcagacag ccacctggca aggctctgga atggctggcc aacatctggt gggatgacga caagtactat aaccccgtcc<br>tgaaaaaccg gctgaccatt agcaaggata cttctaaaaa tcaagtggtg ctgaccatga caaatatgga tcccgttgac<br>accgcaacct actactgcgc ccgcattggt cccataaagt accctacggc accttaccga tatttcgact ttggggcca<br>agggacaatg gttactgtct cg (SEQ ID NO: 26)<br><br>969 gH2 heavy chain (V + constant-hu IgG4P): EVTLKESGPA LVKPTQTLTL<br>TCTFSGFSLT TYGMGVGWIR QPPGKALEWL ANIWWDDDKY YNPSLKNRLT<br>ISKDTSKNQV VLTMTNMDPV DTATYYCARI GPIKYPTAPY RYFDFWGQGT<br>MVTVSSASTK GPSVFPLAPC SRSTSESTAA LGCLVKDYFP EPVTVSWNSG<br>ALTSGVHTFP AVLQSSGLYS LSSVVTVPSS SLGTKTYTCN VDHKPSNTKV<br>DKRVESKYGP CPPPCPAPEF LGGPSVFLFP PKPKDTLMIS RTPEVTCVVV<br>DVSQEDPEVQ FNWYVDGVEV HNAKTKPREE QFNSTYRVVS VLTVLHQDWL<br>NGKEYKCKVS NKGLPSSIEK TISKAKGQPR EPQVYTLPPS QEEMTKNQVS<br>LTCLVKGFYP SDIAVEWESN GQPENNYKTT PPVLDSDGSF FLYSRLTVDK<br>SRWQEGNVFS CSVMHEALHN HYTQKSLSLSLGK (SEQ ID NO: 27)<br><br>969 gH2 heavy chain (V + constant-hu IgG4P, exons underlined):<br>gaagtgacac tcaaggagtc tggacccgct ctggtgaaac caacccaaac actcactttg acatgtactt ttagtggctt<br>ctcattgact acctatggaa tgggcgtggg atggatcaga cagccacctg gcaaggctct ggaatggctg gccaacatct<br>ggtgggatga cgacaagtac tataaccgt ccctgaaaaa ccggctgacc attagcaagg atacttctaa aaatcaagtg<br>gtgctgacca tgacaaatat ggatcccgtt gacaccgcaa cctactactg cgcccgcatt ggtcccataa agtaccctac<br>ggcaccttac cgatatttcg acttttgggg ccaagggaca atggttactg tctcgagcgc ttctacaaag ggcccatccg<br>tcttcccct ggcgccctgc tccaggagca cctccgagag cacagccgcc ctgggctgcc tggtcaagga ctacttcccc<br>gaaccggtga cggtgtcgtg gaactcaggc gccctgacca gcggcgtgca caccttcccg gctgtcctac agtcctcagg<br>actctactcc ctcagcagcg tggtgaccgt gccctccagc agcttgggca cgaagaccta caccgtgcaac gtagatcaca<br>agcccagcaa caccaaggtg gacaagagag ttggtgagag gccagcacag gagggagggg tgtctgctgg aagccaggct<br>cagccctcct gcctggacgc accccggctg tgcagcccca gcccagggca gcaaggcatg cccatctgt ctcctcaccc |

-continued

| Nucleic Acids, Polypeptides |
|---| ggaggcctct gaccacccca ctcatgccca gggagagggt cttctggatt tttccaccag gctccgggca gccacaggct
ggatgcccct accccaggcc ctgcgcatac aggggcaggt gctgcgctca gacctgccaa gagccatatc cgggaggacc
ctgccctga cctaagccca ccccaaaggc caaactctcc actccctgca ctcagacacc ttctctcctc ccagatctga
gtaactccca atcttctctc tgcagagtcc aaatatggtc ccccatgccc accatgccca ggtaagccaa cccaggcctc
gccctccagc tcaaggcggg acaggtgccc tagagtagcc tgcatccagg acaggcccc agccgggtgc tgacgcatcc
acctccatct cttcctcagc acctgagttc ctggggggac catcagtctt cctgttcccc ccaaaaccca aggacactct
catgatctcc cggaccctg aggtcacgtg cgtggtggtg gacgtgagcc aggaagaccc cgaggtccag ttcaactggt
acgtggatgg cgtggaggtg cataatgcca agacaaagcc gcgggaggag cagttcaaca gcacgtaccg tgtggtcagc
gtcctcaccg tcctgcacca ggactggctg aacggcaagg agtacaagtg caaggtctcc aacaaaggcc tcccgtcctc
catcgagaaa accatctcca aagccaaagg tgggacccac ggggtgcgag ggccacatgg acagaggtca gctcggccca
ccctctgccc tgggagtgac cgctgtgcca acctctgtcc ctacagggca gccccgagag ccacaggtgt acaccctgcc
cccatcccag gaggagatga ccaagaacca ggtcagcctg acctgcctgg tcaaaggctt ctaccccagc gacatcgccg
tggagtggga gagcaatggg cagccggaga caactacaa gaccacgcct cccgtgctgg actccgacgg ctccttcttc
ctctacagca ggctaaccgt ggacaagagc aggtggcagg aggggaatgt cttctcatgc tccgtgatgc atgaggctct
gcacaaccac tacacacaga gagcctctcc cctgtctctg ggtaaa (SEQ ID NO: 28)

969 gH2 heavy chain (V +constant-hu IgG4P) with signal sequence underlined and
italicized: *MEWSWVFLFF LSVTTGVHSE* VTLKESGPAL VKPTQTLTLT CTFSGFSLTT
YGMGVGWIRQ PPGKALEWLA NIWWDDDKYY NPSLKNRLTI SKDTSKNQVV
LTMTNMDPVD TATYYCARIG PIKYPTAPYR YFDFWGQGTM VTVSSASTKG
PSVFPLAPCS RSTSESTAAL GCLVKDYFPE PVTVSWNSGA LTSGVHTFPA
VLQSSGLYSL SSVVTVPSSS LGTKTYTCNV DHKPSNTKVD KRVESKYGPP
CPPCPAPEFL GGPSVFLFPP KPKDTLMISR TPEVTCVVVD VSQEDPEVQF
NWYVDGVEVH NAKTKPREEQ FNSTYRVVSV LTVLHQDWLN GKEYKCKVSN
KGLPSSIEKT ISKAKGQPRE PQVYTLPPSQ EEMTKNQVSL TCLVKGFYPS
DIAVEWESNG QPENNYKTTP PVLDSDGSFF LYSRLTVDKS RWQEGNVFSC
SVMHEALHNH YTQKSLSLSL GK (SEQ ID NO: 29)

969 gH2 heavy chain (V + constant-hu IgG4P, exons underlined) with signal
sequence underlined and italicized: *atggagtggt cctgggtgtt tctgttcttc ctgagtgtga ccaccggggt*
*ccactcc*gaa gtgacactca aggagtcggg acccgctctg gtgaaaccaa cccaaacact cactttgaca tgtacttta
gtggctctc attgactacc tatggaatgg gcgtgggatg gatcagacag ccacctggca aggctctgga atggctggcc
aacatctggt gggatgacga caagtactat aacccgtccc tgaaaaaccg gctgaccatt agcaaggata cttctaaaaa
tcaagtggtg ctgaccatga caaatatgga tcccgttgac accgcaacct actactgcgc ccgcattggt cccataaagt
accctacggc accttaccga tatttcgact ttgggggcca agggacaatg ttactgtctc cgagcgcttc tacaaagggc
ccatccgtct tcccctggc gccctgctcc aggagcacct ccgagagcac agccgccctg ggctgcctgg tcaaggacta
cttccccgaa ccggtgacgg tgtcgtggaa ctcaggcgcc ctgaccagcg gcgtgcacac cttcccggct gtcctacagt
cctcaggact ctactccctc agcagcgtgg tgaccgtgcc ctccagcagc ttgggcacga gacctacac ctgcaacgtt
gatcacaagc ccagcaacac caaggtggac aagagagttg tgagaggcc agcacaggga gggagggtgt ctgctggaag
ccaggctcag ccctcctgcc tggacgcacc ccggctgtgc agcccagcc agggcagca aggcatgccc catctgtctc
ctcaccggga ggcctctgac caccccactc atgcccaggg agggtctt ctggattttt ccaccagcc ccgggcagcc
acaggctgga tgcccctacc ccaggccctg cgcatacagg ggcaggtgct gcgctcagac ctgccaagag ccatatccgg
gaggaccctg ccctgacct aagcccaccc caaaggccaa actctccact ccctcagctc agacaccttc tctcctccca
gatctgagta actcccaatc ttctctctgc agagtccaaa tatggtcccc catgccacc atgcccaggt aagccaaccc
aggcctcgcc ctccagctca aggcgggaca ggtgccctag agtagcctgc atccaggaca ggccccagcc gggtgctga
cgcatccacc tccatctctt cctcagcacc tgagttcctg gggggaccat cagtcttcct gttcccccca aaacccaagg
acactctcat gatctcccgg acccctgagg tcacgtgcgt ggtggtggac gtgagccagg aagacccga ggtccagttc
aactggtacg tggatggcgt ggaggtgcat aatgccaaga caaagccgcg ggaggagcag ttcaacagca cgtaccgtgt
ggtcagcgtc ctcaccgtcc tgcaccagga ctggctgaac ggcaaggagt acaagtgcaa ggtctccaac aaaggcctcc
cgtcctccat cgagaaaacc atctccaaag ccaaaggtgg gacccacggg gtgcgagggc cacatggaca gaggtcagct
cggcccaccc tctgccctgg gagtgaccgc tgtgccaacc tctgtcccta gggcagcc cgagagcca ggtgtaca
ccctgccccc atcccaggag gagatgacca agaaccaggt cagcctgacc tgcctggtca aaggcttcta ccccagcgac
atcgccgtgg agtgggagag caatgggcag ccggagaaca actacaagac cacgcctccc gtgctggact ccgacggctc
cttcttcctc tacagcaggc taaccgtgga caagagcagg tggcaggagg gaatgtcttc tcatgctcc gtgatgcatg
aggctctgca caaccactac acacagaaga gcctctccct gtctctgggt aaa (SEQ ID NO: 30)

Human VK1 2-1-(1) O12 JK4 acceptor framework: DIQMTQSPSS LSASVGDRVT
ITCRASQSIS SYLNWYQQKP GKAPKLLIYA ASSLQSGVPS RFSGSGSGTD
FTLTISSLQP EDFATYYCQQ SYSTPLTFGG GTKVEIK (SEQ ID NO: 31)

Human VK1 2-1-(1) O12 JK4 acceptor framework: gacatccaga tgacccagtc tccatcctcc
ctgtctgcat ctgtaggaga cagagtcacc atcacttgcc gggcaagtca gagcattagc agctatttaa attggtatca
gcagaaacca gggaaagccc ctaagctcct gatctatgct gcatccagtt tgcaaagtgg ggtcccatca aggttcagtg
gcagtggatc tgggacagat ttcactctca ccatcagcag tctgcaacct gaagattttg caacttacta ctgtcaacag
agttacagta cccctctcac tttcggcgga gggaccaagg tggagatcaa a (SEQ ID NO: 32)

Human VH2 3-1 2-70 JH3 acceptor framework: QVTLKESGPA LVKPTQTLTL
TCTFSGFSLS TSGMRVSWIR QPPGKALEWL ARIDWDDDKF YSTSLKTRLT
ISKDTSKNQV VLTMTNMDPV DTATYYCARI AFDIWGQGTM VTVS (SEQ ID NO: 33)

Human VH2 3-1 2-70 JH3 acceptor framework: caggtcacct tgaaggagtc tggtcctgcg
ctggtgaaac ccacacagac cctcacactg acctgcacct tctctgggtt ctcactcagc actagtggaa tgcgtgtgag
ctggatccgt cagcccccag ggaaggccct ggagtggctt gcacgcattg attgggatga tgataaattc tacagcacat
ctctgaagac caggctcacc atctccaagg acacctccaa aaaccaggtg gtccttacaa tgaccaacat ggaccctgtg
gacacagcca cgtattactg tgcacggata gcttttgata tctggggcca agggacaatg gtcaccgtct ct (SEQ ID NO: 34)

-continued

Nucleic Acids, Polypeptides

```
Amino acid sequence for CSF-1R: MGPGVLLLLL VATAWHGQGI PVIEPSVPEL
VVKPGATVTL RCVGNGSVEW DGPPSPHWTL YSDGSSSILS TNNATFQNTG
TYRCTEPGDP LGGSAAIHLY VKDPARPWNV LAQEVVVFED QDALLPCLLT
DPVLEAGVSL VRVRGRPLMR HTNYSFSPWH GFTIHRAKFI QSQDYQCSAL
MGGRKVMSIS IRLKVQKVIP GPPALTLVPA ELVRIRGEAA QIVCSASSVD
VNFDVFLQHN NTKLAIPQQS DFHNNRYQKV LTLNLDQVDF QHAGNYSCVA
SNVQGKHSTS MFFRVVESAY LNLSSEQNLI QEVTVGEGLN LKVMVEAYPG
LQGFNWTYLG PFSDHQPEPK LANATTKDTY RHTFTLSLPR LKPSEAGRYS
FLARNPGGWR ALTFELTLRY PPEVSVIWTF INGSGTLLCA ASGYPQPNVT
WLQCSGHTDR CDEAQVLQVW DDPYPEVLSQ EPFHKVTVQS LLTVETLEHN
QTYECRAHNS VGSGSWAFIP ISAGAHTHPP DEFLFTPVVV ACMSIMALLL
LLLLLLLYKY KQKPKYQVRW KIIESYEGNS YTFIDPTQLP YNEKWEFPRN
NLQFGKTLGA GAFGKVVEAT AFGLGKEDAV LKVAVKMLKS TAHADEKEAL
MSELKIMSHL GQHENIVNLL GACTHGGPVL VITEYCCYGD LLNFLRRKAE
AMLGPSLSPG QDPEGGVDYK NIHLEKKYVR RDSGFSSQGV DTYVEMRPVS
TSSNDSFSEQ DLDKEDGRPL ELRDLLHFSS QVAQGMAFLA SKNCIHRDVA
ARNVLLTNGH VAKIGDFGLA RDIMNDSNYI VKGNARLPVK WMAPESIFDC
VYTVQSDVWS YGILLWEIFS LGLNPYPGIL VNSKFYKLVK DGYQMAQPAF
APKNIYSIMQ ACWALEPTHR PTFQQICSFL QEQAQEDRRE RDYTNLPSSS
RSGGSGSSSS ELEEESSSEH LTCCEQGDIA QPLLQPNNYQ FC (SEQ ID NO:  35)

Amino acid sequence for CSF-1R:
MRHTNYSFSPWHGFTIHRAKFIQSQDYQCSALMGGRKVMSISIRLKVQK (SEQ ID NO:
36)

Amino acid sequence for CSF-1R: (SNP V32G, A245S, H247P, V279M, position
underlined)
IPVIEPSVPELVVKPGATVTLRCVGNGSVEWDGPPSPHWTLYSDGSSSILSTNNATFQN
TGTYRCTEPGDPLGGSAAIHLYVKDPARPWNVLAQEVVVFEDQDALLPCLLTDPVLE
AGVSLVRVRGRPLMRHTNYSFSPWHGFTIHRAKFIQSQDYQCSALMGGRKVMSISIRL
KVQKVIPGPPALTLVPAELVRIRGEAAQIVCSASSVDVNFDVFLQHNNTKLAIHQQSDF
HNNRYQKVLTLNLDQVDFQHAGNYSCVASNVQGKHSTSMFFRVVESAYLNLSSEQN
LIQEVTVGEGLNLKVMVEAYPGLQGFNWTYLGPFSDHQPEPKLANATTKDTYRHTFT
LSLPRLKPSEAGRYSFLARNPGGWRALTFELTLRYPPEVSVIWTFINGSGTLLCAASGY
PQPNVTWLQCSGHTDRCDEAQVLQVWDDPYPEVLSQEPFHKVTVQSLLTVETLEHNQ
TYECRAHNSVGSGSWAFIPISAGAHTHPPDE (SEQ ID NO: 37)

MGPGVLLLLL VATAWHGQGI PVIEPSVPEL VVKPGATVTL RCVGNGSVEW
DGPPSPHWTL YSDGSSSILS TNNATFQNTG TYRCTEPGDP LGGSAAIHLY
VKDPARPWNV LAQEVVVFED QDALLPCLLT DPVLEAGVSL VRVRGRPLMR
HTNYSFSPWH GFTIHRAKFI QSQDYQCSAL MGGRKVMSIS IRLKVQKVIP
GPPALTLVPA ELVRIRGEAA QIVCSASSVD VNFDVFLQHN NTKLAIPQQS
DFHNNRYQKV LTLNLDQVDF QHAGNYSCVA SNVQGKHSTS MFFRVVESAY
LNLSSEQNLI QEVTVGEGLN LKVMVEAYPG LQGFNWTYLG PFSDHQPEPK
LANATTKDTY RHTFTLSLPR LKPSEAGRYS FLARNPGGWR ALTFELTLRY
PPEVSVIWTF INGSGTLLCA ASGYPQPNVT WLQCSGHTDR CDEAQVLQVW
DDPYPEVLSQ EPFHKVTVQS LLTVETLEHN QTYECRAHNS VGSGSWAFIP
ISAGAHTHPP DE (SEQ ID NO: 38)
```

Anti-CSF-1 Antibody

The present disclosure also provides, suitable for any methods and combination therapies disclosed herein, an antibody and antigen-binding fragment thereof that specifically binds to a CSF-1, preferably human CSF-1, and that functions to inhibit CSF-1. CSF-1 expression correlates with poor diagnosis and tumor progression in many cancer types. Increased level of CSF-1 is associated with increased levels of tumor-associated macrophages, which are a major factor of tumor stroma and poor disease prognosis. In some embodiments, the anti-CSF-1 antibody or antigen fragment thereof, inhibits the activity of CSF-1. In some embodiments, the anti-CSF-1 antibody inhibits the binding of a CSF-1 to c-fms receptor and blocks or prevents activation of c-fms. In some embodiments, the anti-CSF-1 antibody or antigen binding fragment thereof is a humanized and/or human anti-CSF-1 antibody or fragment thereof. In some embodiments, human anti-CSF-1 antibodies are produced by immunizing a non-human transgenic animal, e.g., a rodent, whose genome comprises human immunoglobulin genes so that the rodent produces human antibodies. Antibodies to CSF-1 are known in the art. Antibodies that preferably inhibit CSF-1 activity include those disclosed in U.S. Pat. No. 8,652,469 B2 and WO2013068902, the contents of each of which are hereby incorporated by reference in their entireties. For example, antibodies that inhibit CSF-1 include MCS110.

In some embodiments, the anti-CSF-1 antibody or antigen binding fragment thereof comprises a binding affinity for human CSF-1 of 100 μM or less, or 10 μM or less. In some embodiments, the anti-CSF-1 antibody or antigen binding fragment thereof is administered at a dose ranging between about 0.1 mg/kg and about 30 mg/kg.

Inhibitors of CSF-1R

The present disclosure also provides, suitable for any methods and combination therapies disclosed herein, an inhibitor of CSF-1R activity, preferably human CSF-1R, that functions to inhibit CSF-1R activity. The term "CSF-1R activity" as used herein refers to the spectrum of activity understood in the art for CSF-1R, in particular the activity of human CSF-1R and isoforms thereof, for example 1, 2, 3 or all isoforms. For example, binding of ligand to the receptor induces phosphorylation of CSF-1R at specific tyrosine residues (Bourette R P and Rohrschneider L R, 2000, Growth Factors17: 155-166) and the ensuing cascade of signal transduction events can mediate cell migration, survival, differentiation and proliferation (Suzu Setal, 1997, J Immunol, 159, 1860-7; Yeung Y-G and Stanley E R, 2003, Mol Cell Proteomics, 2, 1143-55; Yu W et al 2008, J Leukoc Bio184(3), 852-63). Expression in transfected cells of mutant CSF-1R receptor molecules comprising phenylalanine residues in place of selected tyrosine residues revealed the association of specific tyrosine residues with cellular outcomes such as survival, proliferation and morphology (Yu et al J Leukoc Biol 2008 Sep. 84(3): 852-863). Proteomic approaches and immunoblotting techniques using anti-phosphotyrosine antibodies together with molecule specific antibodies, have identified a number of the intracellular molecules involved in mediating these cell functions following ligand stimulation of the receptor (Yeung Y-G et al, 1998, J Biol Chem. 13, 273(46): 17128-37; Husson H et al, 1997, Oncogene15, 14(19): 2331-8.

An inhibitor of CSF-1R activity according to the present disclosure is an agent that interferes with, for example reduces/inhibits or blocks the activity of CSF-1R. Particularly preferred are agents which interfere with the activity of CSF-1R. Inhibitors according to the present disclosure may partially or completely inhibit CSF-1R activity. Inhibitors suitable for the methods and combination therapies of the present disclosure include without limitation, inhibitors that are capable of interacting with (e.g. binding to, or recognizing) IL-34, CSF-1 or the CSF-1 receptor (CSF-1R) or a nucleic acid molecule encoding IL-34, CSF-1 or CSF-1R, or are capable of inhibiting the expression of IL-34, CSF-1 or CSF-1 R or are capable of inhibiting the interaction between CSF-1R and CSF-1 and/or IL-34. Such inhibitors may be, without limitation, antibodies, nucleic acids (e.g. DNA, RNA, antisense RNA and siRNA), carbohydrates, lipids, proteins, polypeptides, peptides, peptidomimetics, small molecules and other drugs.

In some embodiments, the inhibitor of CSF-1R activity is a small chemical entity or a small molecule CSF-1R inhibitor. In one embodiment the inhibitor blocks binding of CSF-1 to the receptor CSF-1R. In some embodiments, the inhibitor is a highly-selective small molecule CSF-1R inhibitor. Examples of small molecule CSF-1R inhibitors include, but are not limited to, DCC-3014, ARRY-382, GW2580, BLZ94, PLX3397, PLX7386, JNJ-40346527, Imatinib, dasatinib, sunitinib, CEP-701, and PKC-412. Other examples of small molecule CSF-1R inhibitors are described in, e.g., Ramachandran et al., Bioorganic & Medicinal Chemistry Letters, 2017, 27(10): 2153-2160; Mashkani et al., Bioorganic & Medicinal Chemistry, 2010, 18(5): 1789-1797; and Patel et al., Curr Top Med Chem. 2009, 9(7):599-610, the contents of each of which are incorporated herein by reference in their entireties.

Examples, of suitable inhibitors include, but are not limited to, a synthetic functional fragment of the CSF-1 receptor that binds to CSF-1 and interferes with binding to the native CSF-1 receptor, a synthetic functional fragment of CSF-1 that binds to CSF-1 receptor and interferes with binding to the native CSF-1 receptor, a synthetic functional fragment of IL-34 that binds to CSF-1 receptor and interferes with binding to the native CSF-1 receptor, an antibody that binds to CSF-1 or IL-34 or to the CSF-1 receptor and interferes with CSF-1 receptor-ligand interaction, an antisense nucleic acid molecule that specifically hybridizes to mRNA encoding CSF-1, IL-34 or the CSF-1 receptor or a small molecule or other drug which inhibits the activity ofiL-34, CSF-1 or CSF-1R. Inhibitors of CSF-1 receptor activity are known in the art as are methods of identifying and producing such inhibitors. Neutralizing anti-CSF-1 antibodies have been described, for example by Weir et al., 1996, J Bone Miner. Res. 11, 1474-1481 and Haran-Ghera et al, 1997, Blood, 89, 2537-2545, which also describes anti-CSF-1R antibodies. Antisense antagonists of CSF-1 have also been described (EP1223980).

Agents that may be suitable inhibitors can be selected from a wide variety of candidate agents. Examples of candidate agents include but are not limited to, nucleic acids (e.g. DNA and RNA), carbohydrates, lipids, proteins, polypeptides, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683). Examples of suitable methods based on the present description for the synthesis of molecular libraries can be found in the art, for example in: DeWitt et al, 1993, Proc. Natl. Acad. Sci. USA 90:6909; Erb et al, 1994, Proc. Natl. Acad. Sci. USA 91: 11422; Zuckermann et al, 1994, J. Med. Chem. 37:2678; Cho et al, 1993, Science 261:1303; Carrell et al, 1994, Angew. Chem. hit. Ed. Engl. 33:2059; Carell et al, 1994, Angew. Chem. Int. Ed. Engl. 33:2061; and Gallop et al, 1994, J. Med. Chem. 37:1233. Libraries of compounds maybe presented, for example, in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223, 409), spores (U.S. Pat. Nos. 5,571,698; 5,403,484; and 5,223,409), plasmids (Cull et al, 1992, Proc. Natl. Acad. Sci. USA 89:1865-1869) or phage (Scott and Smith, 1990, Science 249:386-390; Devlin, 1990, Science 249:404-406; Cwirla et al, 1990, Proc. Natl. Acad. Sci. USA 87:6378-6382; and Felici, 1991, J. Mol. Biol. 222:301-310).

Histone Deacetylase

Cancer, tumors, tumor-related disorders, and neoplastic disease states are serious and often times life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm.

The HDACs are a family including at least eighteen enzymes, grouped in three classes (Class I, II and III). Class I HDACs include, but are not limited to, HADCs 1, 2, 3, and 8. Class I HDACs can be found in the nucleus and are believed to be involved with transcriptional control repressors. Class II HDACs include, but are not limited to, HDACS 4, 5, 6, 7, and 9 and can be found in both the cytoplasm as well as the nucleus. Class III HDACs are believed to be NAD dependent proteins and include, but are not limited to, members of the Sirtuin family of proteins. Non-limiting examples of sirtuin proteins include SIRT1-7. As used herein, the term "selective HDAC" refers to an HDAC inhibitor that does not interact with all three HDAC classes.

HDAC Inhibitors

HDAC inhibitors are an emerging class of therapeutic agents that promote differentiation and apoptosis in hematologic and solid malignancies through chromatin remodeling and gene expression regulation. Several HDAC inhibitors have been identified including benzamides (e.g., entinostat), short-chain fatty acids (e.g., Sodium phenylbutyrate); hydroxamic acids (e.g., suberoylanilide hydroxamic acid and trichostatin A); cyclic tetrapeptides containing a 2-amino-8-oxo-9, 10-epoxy-decanoyl moiety (e.g., trapoxin A) and cyclic peptides without the 2-amino-8-oxo-9, 10-epoxy-decanoyl moiety (e.g., FK228). Entinostat is a benzamide HDAC inhibitor undergoing clinical investigation in multiple types of solid tumors and hematologic cancers. Entinostat is rapidly absorbed and has a half-life of about 100 hours and, importantly, changes in histone acetylation persist for several weeks following the administration of entinostat.

HDAC inhibitors can be classified broadly into pan HDAC inhibitors and selective HDAC inhibitors. Although there is a large structural diversity of known HDAC inhibitors, they share common features: a part that interacts with the enzyme active site and a side-chain that sits inside the channel leading to the active site. This can be seen with the hydroxamates such as SAHA, where the hydroxamate group is believed to interact with the active site. In the case of the depsipeptides, it is believed that an intracellular reduction of the disulphide bond creates a free thiol group (which interacts with the active site) attached to a 4-carbon alkenyl chain. A difference between the HDAC inhibitors is in the way that they interact with the rim of the HDAC channel, which is at the opposite end of the channel to the active site. It is this interaction, between the HDAC inhibitor and the rim of the channel, which is believed to account, at least in part, for some observed differences in HDAC selectivity between pan-HDAC inhibitors, such as SAHA and selective HDAC inhibitors such as the depsipeptides. A particularly preferred HDAC inhibitor is entinostat. Entinostat has the chemical name N-(2-aminophenyl)-4-[N-(pyridine-3-yl)methoxycarbonylamino-methyl]-benzamide and the chemical structure shown below. In one aspect, the present disclosure provides a combination comprising an anti-CSF-1R antibody or anti-CSF-1 antibody or antigen binding fragment thereof or an inhibitor of CSF-1R activity and an HDAC inhibitor, e.g., entinostat.

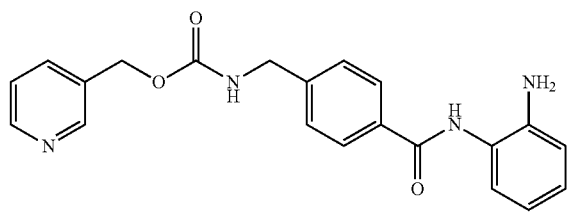

Chemical structure of entinostat

Formulations and Methods of Treatment

Any antibody (e.g., an anti-CSF-1R antibody or anti-CSF-1 antibody) disclosed herein can be used for the methods, kits, compositions or combination therapy of the disclosure.

In some embodiments, a pharmaceutical composition of the disclosure comprises an anti-CSF-1R antibody or anti-CSF-1 antibody or antigen binding fragment thereof or an inhibitor of CSF-1R activity and a pharmaceutically acceptable carrier.

The anti-CSF-1R antibody or anti-CSF-1 antibody or inhibitor of CSF-1R activity is suitable for administration as part of a combination therapy with an HDAC inhibitor. For example, the anti-CSF-1R antibody or anti-CSF-1 antibody or antigen binding fragment thereof or inhibitor of CSF-1R activity, is suitable for administration as part of a combination therapy with one or more HDAC inhibitor (such as a entinostat), suitable to be administered together, sequentially, or in alternation. The disclosure also relates to a combination of a pharmaceutical composition comprising a therapeutically effective amount of an anti-CSF-1R antibody or anti-CSF-1 antibody or antigen binding fragment thereof or inhibitor of CSF-1R activity and a pharmaceutically acceptable carrier and a pharmaceutical composition comprising a therapeutically effective amount of an HDAC inhibitor and a pharmaceutically acceptable carrier.

In some embodiments, the anti-CSF-1R antibody or anti-CSF-1 antibody or antigen binding fragment thereof or inhibitor of CSF-1R activity and the HDAC inhibitor (e.g., entinostat) are formulated into a single therapeutic composition, and the anti-CSF-1R or anti-CSF-1 antibody or antigen binding fragment thereof or inhibitor of CSF-1R activity and the HDAC inhibitor (e.g., entinostat) are administered simultaneously.

In some embodiments, the anti-CSF-1R antibody or anti-CSF-1 antibody or antigen binding fragment thereof or inhibitor of CSF-1R activity and the HDAC inhibitor (e.g., entinostat) are separate from each other, e.g., each is formulated into a separate therapeutic composition, and the anti-CSF-1R antibody or anti-CSF-1 antibody or antigen binding fragment thereof or inhibitor of CSF-1R activity and the HDAC inhibitor (e.g., entinostat) are administered simultaneously, or the anti-CSF-1R or anti-CSF-1 antibody or antigen binding fragment thereof or the inhibitor of CSF-1R activity and the HDAC inhibitor comprising entinostat are administered at different times during a treatment regimen.

For example, the anti-CSF-1R antibody or anti-CSF-1 antibody or antigen binding fragment thereof or inhibitor of CSF-1R activity is administered prior to or concurrently with the administration of the HDAC inhibitor (e.g., entinostat), e.g., to treat cancer. In another example, the anti-CSF-1R antibody or anti-CSF-1 antibody or antigen binding fragment thereof or inhibitor of CSF-1R activity is administered subsequent to the administration of the HDAC inhibitor (e.g., entinostat), e.g., to treat cancer. Alternatively, the anti-CSF-1R antibody or anti-CSF-1 antibody or antigen binding fragment thereof or inhibitor of CSF-1R activity and the HDAC inhibitor (e.g., entinostat) are administered in an alternating fashion. As described herein, the anti-CSF-1R antibody or anti-CSF-1 antibody or antigen binding fragment thereof or inhibitor of CSF-1R activity and the HDAC inhibitor comprising entinostat are administered in single doses or in multiple doses.

In certain embodiments, the combinations described herein are used for treating cancer or a cell proliferative disorder in a subject in need thereof.

As used herein, "abnormal cell growth," refers to cell growth that is independent of normal regulatory mechanisms (e.g., loss of contact inhibition), including the abnormal growth of normal cells and the growth of abnormal cells.

"Neoplasia" as described herein, is an abnormal, unregulated and disorganized proliferation of cells that is distinguished from normal cells by autonomous growth and somatic mutations. As neoplastic cells grow and divide they pass on their genetic mutations and proliferative characteristics to progeny cells. A neoplasm, or tumor, is an accumulation of neoplastic cells. In some embodiments, the neoplasm can be benign or malignant.

"Metastasis," as used herein, refers to the dissemination of tumor cells via lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

As discussed herein, "angiogenesis" is prominent in tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors such as renal cell carcinoma, hepatocellular carcinoma, and benign tumors such as acoustic neuroma, and neurofibroma. Angiogenesis has been associated with blood-born tumors such as leukemias. It is believed that angiogenesis plays a role in the abnormalities in the bone marrow that give rise to leukemia. Prevention of angiogenesis could halt the growth of cancerous tumors and the resultant damage to the subject due to the presence of the tumor.

As used herein, the term "cell proliferative disorder" refers to conditions in which unregulated or abnormal growth, or both, of cells can lead to the development of an unwanted condition or disease, which may or may not be cancerous. Exemplary cell proliferative disorders encompass a variety of conditions wherein cell division is deregulated. Exemplary cell proliferative disorder includes, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute lymphocytic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

In some embodiments, the cancer is acute myeloid leukemia (AML), acute lymphoblastic leukemia (ALL), chronic lymphoblastic leukemia (CALL), non-Hodgkin lymphoma (NHL), multiple myeloma, mantle cell lymphoma (MCL), diffuse large b-cell lymphoma (DLBCL), primary mediastinal b-cell lymphoma (PFBC), or transformed follicular lymphoma (TFF). In some embodiments, the cancer is mesothelioma, pancreatic cancer, glioma, neuroblastoma, ovarian cancer, glioblastoma, myelodysplastic syndromes (MDS), breast cancer, prostate cancer, colorectal cancer, skin cancer, oesophageal cancer, esophageal cancer, gastric cancer, astrocytic cancer, endometrial cancer, cervical cancer, bladder cancer, renal cancer, lung cancer, liver cancer, thyroid cancer, or head and neck cancer.

The terms "treat," "treating," and "treatment" are meant to include alleviating or abrogating a disorder, disease, or condition; or one or more of the symptoms associated with the disorder, disease, or condition; or alleviating or eradicating the cause(s) of the disorder, disease, or condition itself. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions disclosed herein leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with the combination of this disclosure comprising anti-CSF-1R antibody or anti-CSF-1 antibody or antigen binding fragment thereof or inhibitor of CSF-1R activity and the HDAC inhibitor (e.g., entinostat).

A "pharmaceutical composition" or "therapeutic composition" is a formulation containing the active ingredient, such as an anti-CSF-1R antibody or anti-CSF-1 antibody or antigen binding fragment thereof or inhibitor of CSF-1R activity or an HDAC inhibitor disclosed herein in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

"Active ingredient" as employed herein refers to an ingredient with a pharmacological effect, such as a therapeutic effect, at a relevant dose.

"Pharmaceutically acceptable carrier" means a carrier that is useful in preparing a pharmaceutical composition that is generally safe, non-toxic and neither biologically nor otherwise undesirable, and includes excipient that is acceptable for veterinary use as well as human pharmaceutical use. For example, the pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid.

Once formulated, the compositions of the disclosure can be administered directly to the subject.

In certain embodiments, the pH of the final formulation is not similar to the value of the isoelectric point (pI) of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

In one example, the pharmaceutical formulation at a pH in the range of 4.0 to 7.0 comprises: 1 to 200 mg/mL of an antibody according to the present disclosure, 1 to 100 mM of a buffer, 0.001 to 1% of a surfactant, a) 10 to 500 mM of a stabilizer, b) 10 to 500 mM of a stabilizer and 5 to 500 mM of a tonicity agent, or c) 5 to 500 mM of a tonicity agent.

The pharmaceutical compositions of this disclosure may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the disclosure. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, and maltose), oligo- and polysaccharides (e.g. dextrans), polyalcohols (e.g. sorbitol, mannitol, and xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilizers, surface-active agents (surfactants), antioxidants, lubricants and means for adjusting the pH. All these ingredients are known in the art.

The propellant-gas-containing inhalable aerosols according to the disclosure may contain up to 5% by weight of active substance. Aerosols according to the disclosure contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the disclosure can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilized antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein may be suitable for delivery via nebulization.

It is also envisaged that the antibody of the present disclosure may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The pharmaceutical compositions suitably comprise a therapeutically effective amount of the anti-CSF-1R antibody or anti-CSF-1 antibody or antigen binding fragment thereof or inhibitor of CSF-1R activity and the HDAC inhibitor (e.g., entinostat). The term "therapeutically effective amount" as used herein refers to an amount of a therapeutic agent needed to treat, ameliorate or prevent a targeted disease or condition, or to exhibit a detectable therapeutic, pharmacological or preventative effect. For example, for any antibody or the HDAC inhibitor (e.g., entinostat) disclosed herein, the therapeutically effective amount can be estimated initially either in cell culture assays, e.g., of neoplastic cells, or in animal models, usually rats, mice, rabbits, dogs, pigs or primates. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Generally, the dose should be sufficient to result in slowing, and preferably regressing, the growth of the tumors and preferably causing complete regression of the cancer. Dosages can range from about 0.01 mg/kg per day to about 10 mg/kg per day. In some embodiments, dosages can range from about 0.1 mg/kg, 0.5 mg/kg, 1 mg/kg, 1.5 mg/kg, 3 mg/kg, 5 mg/kg, 6 mg/kg, 7.5 mg/kg, or about 10 mg/kg. In some embodiments, the dose will be in the range of about 0.1 mg/day to about 5 mg/kg; about 0.1 mg/day to about 10 mg/kg; about 0.1 mg/day to about 20 mg/kg; about 0.1 mg to about 30 mg/kg; or about 0.1 mg to about 40 mg/kg or about 0.1 mg to about 50 mg/kg or in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount of the anti-CSF-1R antibody or anti-CSF-1 antibody or antigen binding fragment thereof or inhibitor of CSF-1R activity of this disclosure will be from about 0.01 mg/kg to about 500 mg/kg, for example, about 0.1 mg/kg to about 200 mg/kg (such as about 100 mg/kg), or about 0.1 mg/kg to about 10 mg/kg (such as about 0.1 mg/kg, 0.5 mg/kg, 1 mg/kg, 1.5 mg/kg, 3 mg/kg, 5 mg/kg, 6 mg/kg, 7.5 mg/kg, or about 10 mg/kg). In certain embodiments, the effective amount of the anti-CSF-1R antibody or anti-CSF-1 antibody or antigen binding fragment thereof or inhibitor of CSF-1R activity is about 3 mg/kg or about 6 mg/kg.

In some embodiments, entinostat is administered periodically during the treatment cycle. In some embodiments, entinostat is administered on day 1 of the treatment cycle. In some embodiments, entinostat is administered orally. In some embodiments, entinostat is administered weekly. In some embodiments, entinostat is administered every two weeks. In some embodiments, entinostat is administered at a dose of 3 mg. In some embodiments, entinostat is administered at a dose of 5 mg. In some embodiments, entinostat is administered at a dose of 10 mg. In some embodiments, entinostat is administered orally once every week during the treatment cycle at a dose of 3 mg. In some embodiments, entinostat is administered orally once every week during the treatment cycle at a dose of 5 mg. In some embodiments, entinostat is administered orally once every two weeks during the treatment cycle at a dose of 10 mg. In some embodiments, entinostat is administered prior to the administration of anti-CSF-1R antibody or anti-CSF-1 antibody or antigen binding fragment thereof or inhibitor of CSF-1R activity. In some embodiments, entinostat is administered after the administration of anti-CSF-1R antibody or antigen binding fragment thereof. In some embodiments, entinostat is administered simultaneously as the administration of anti-CSF-1R antibody or anti-CSF-1 antibody or antigen binding fragment thereof or inhibitor of CSF-1R activity.

Pharmaceutical compositions may be conveniently presented in unit dose forms containing a predetermined amount of an active agent of the disclosure per dose.

Therapeutic doses of the antibodies (e.g., anti-CSF-1R antibodies or anti-CSF-1 antibody) according the present disclosure show no apparent or limited toxicology effects in vivo.

Long-acting pharmaceutical compositions may be administered every 3 to 4 days, every week, or once every two weeks depending on half-life and clearance rate of the particular formulation. In some embodiments, the anti-CSF-1R antibody or anti-CSF-1 antibody or antigen binding fragment thereof or inhibitor of CSF-1R activity is administered at least every other day, every week, every 2 weeks or every month. In certain embodiments, the pulsed dose (e.g., of anti-CSF-1R antibody) is administered every week or every 2 weeks. In certain embodiments, the anti-CSF-1R antibody or anti-CSF-1 antibody or antigen binding fragment thereof or inhibitor of CSF-1R activity and the HDAC inhibitor (e.g., entinostat) are administered at the same frequency, either simultaneously or sequentially, e.g., every 1 or 2 weeks but the administration of each therapy is separated by at least 1 hour, 2 hours, 3 hours, 4 hours, 5 hours, 6 hours, 8 hours, 10 hours, 12 hours, 14 hours, 16 hours, 18 hours, 20 hours, 24 hours, 1 day, 2 days, 3 days, 4 days, 5 days, 6 days, or at least 7 days.

In certain embodiments, the anti-CSF-1R antibody or anti-CSF-1 antibody or antigen binding fragment thereof or inhibitor of CSF-1R activity and the HDAC inhibitor (e.g., entinostat) are administered at different frequencies and each independently is administered every day, every other day, every week, every 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or every 20 weeks, or every month.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half-life (e.g. 2 to 15 days) and/or long lasting pharmacodynamics (PD) profile it may only be necessary to give a dosage once per day, once per week or even once every 1 or 2 months.

Half-life as employed herein is intended to refer the duration of the molecule in circulation, for example in serum/plasma.

Compositions or therapies disclosed herein may be administered individually to a patient or may be administered in combination (e.g. simultaneously, sequentially or separately).

In some embodiments, the HDAC inhibitor (e.g., entinostat) and the second agent (e.g., anti-CSF-1R antibody or anti-CSF-1 antibody or antigen binding fragment thereof, or an inhibitor of CSF-1R activity) are administered in temporal proximity (e.g., the HDAC inhibitor (e.g., entinostat) and the second agent (e.g., anti-CSF-1R antibody or anti-CSF-1 antibody or antigen binding fragment thereof, or an inhibitor of CSF-1R activity) can be administered simultaneously). Accordingly, the present disclosure provides a method of treating or preventing cancer comprising administering an HDAC inhibitor (e.g., entinostat) and a second agent (e.g., an anti-CSF-1R antibody or antigen binding fragment thereof, an anti-CSF-1 antibody or antigen binding fragment thereof, or an inhibitor of CSF-1R activity) in temporal proximity.

In some embodiments, "temporal proximity" means that administration of one therapeutic agent occurs within a time period before or after the administration of another therapeutic agent, such that the therapeutic effect of the one therapeutic agent overlaps with the therapeutic effect of the another therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

"Combination therapy" is intended to embrace administration of the therapeutic agents disclosed herein in a sequential or simultaneous manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. Therapeutic agents may also be administered in alternation.

The combinations and methods disclosed herein (e.g., those comprising an anti-CSF-1R or anti-CSF-1 antibody or antigen binding fragment thereof or an inhibitor of CSF-1R activity and an HDAC inhibitor) may further include treatments wherein they are supplemented with one or more therapeutic agents or therapies, e.g., radiation therapy, surgery, or anti-cancer agents or chemotherapy. Treatments that can be used to supplement the combinations and methods disclosed herein include, but are not limited to, alkylating/DNA-damaging agents (e.g. carboplatin, cisplatin), antimetabolites (e.g. capecitabine, gemcitabine, 5-fluorouracil), mitotic inhibitors (e.g. paclitaxel, vincristine), IL-2, sipuleucel-T, talimogene laherparepvec, peginterferon alfa-2a, as well as antibody ingredients (for example epidermal growth factor receptor family (EGFR, HER-2), vascular endothelial growth factor receptors (VEGFR), platelet derived growth factor receptor (PDGFR) antibodies, such as nivolumab, ipilimumab, atezolizumab, elotuzumab, daratumumab, pembrolizumab, ramucirumab, brentuximab, brentuximab vedotin, ofatumumab, denosumab, and combinations thereof), or non-antibody ingredients, such as imatinib, dasatinib, nilotinib, bosutinib, gefitinib, erlotinib, temsirolimus, vandetanib, vemurafenib, crizotinib, vorinostat, romidepsin, bortezomib, sorafenib, sunitinib, pazopanib, regorafenib, cabozantinib, pirfenidone, steroids or other drug molecules, in particular drug molecules whose half-life is independent of CSF-1R binding.

As used herein, a "subject in need thereof" is a subject suffering from a cell proliferative disorder or having an increased risk of developing such disorder relative to the population at large. A subject in need thereof can have a precancerous condition. A "subject" includes a mammal. The mammal can be e.g., any mammal, e.g., a human, primate, bird, mouse, rat, fowl, dog, cat, cow, horse, goat, camel, sheep or pig. Preferably, the mammal is a human.

The term "antibody" is used according to its commonly known meaning in the art. The antibody molecules of the present disclosure may comprise a complete antibody molecule having full length heavy and light chains or a binding fragment thereof and may be, but are not limited to Fab, modified Fab, Fab', modified Fab', F(ab')$_2$, Fv, single domain antibodies (e.g. VH or VL or VHH), scFv, bi, tri or tetravalent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews-Online 2(3), 209-217). The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in International patent applications WO05/003169, WO05/003170 and WO05/003171.

Multi-valent antibodies may comprise multiple specificities e.g. bispecific or may be monospecific (see for example WO92/22853, WO05/113605, WO2009/040562 and WO2010/035012).

Binding fragment of an antibody as employed herein refers to a fragment capable of binding an antigen with affinity to characterize the fragment as specific for the antigen.

In one embodiment the antibody according to the present disclosure is provided as CSF-1R binding antibody fusion protein which comprises an immunoglobulin moiety, for example a Fab or Fab' fragment, and one or two single domain antibodies (dAb) linked directly or indirectly thereto, for example as described in WO2009/040562, WO2010/035012, WO2011/030107, WO2011/061492 and WO2011/086091, all incorporated herein by reference.

In some embodiments, the fusion protein comprises two domain antibodies, for example as a variable heavy (VH) and variable light (VL) pairing, optionally linked by a disulfide bond. In some embodiments, the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multi-valent fusion protein according to the present disclosure has an albumin binding site, for example a VH/VL pair therein provides an albumin binding site.

The constant region domains of the antibody molecule of the present disclosure, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995). Accordingly, the C-terminal lysine of the antibody heavy chain may be absent.

As used herein, the term 'humanized antibody refers to an antibody or antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody) (see, e.g. U.S. Pat. No. 5,585,089; WO91/09967). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36:25-34). In one embodiment only the specificity determining residues from one or more of the CDRs described herein above are transferred to the human antibody framework. In another embodiment only the specificity determining residues from each of the CDRs described herein above are transferred to the human antibody framework. When the CDRs or specificity determining residues are grafted, any appropriate, acceptor variable region framework sequence may be used having regard to the class/type of the donor antibody from which the CDRs are derived, including mouse, primate and human framework regions.

As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean+/−10% of the recited value.

Articles used in the claims and description, such as "a," "an," and "the," may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all, of the group members are present in, employed in, or otherwise relevant to a given product or process.

It is also noted that the term "comprising" is intended to be open and permits but does not require the inclusion of additional elements or steps. When the term "comprising" is used herein, the terms "consisting essentially of" and "consisting of" are thus also encompassed and disclosed. Throughout the description, where compositions or combinations are described as having, including, or comprising specific components or steps, it is contemplated that compositions or combinations also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Where technically appropriate, embodiments of the invention may be combined. Any embodiments specifically and explicitly recited herein may form the basis of a disclaimer either alone or in combination with one or more further embodiments.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same.

EXAMPLES

Example 1

A first analysis of entinostat in combination with anti-CSF-1R (Ab535) is evaluated in CT26 colon cancer model and the evaluation of immune cell profiling of Tumor infiltrating lymphocytes (TIL). Entinostat has been shown in preclinical models to reduce the number of, and inhibit the function of, host immune suppressor cells in order to enhance the anti-tumor activity of immune checkpoint blockade. The study was carried out to test whether entinostat combined with murine anti-CSF-1R (Ab535) results in an improved overall response rate for the combination compared to either agent alone.

Experimental Design and Results

Figure 2:
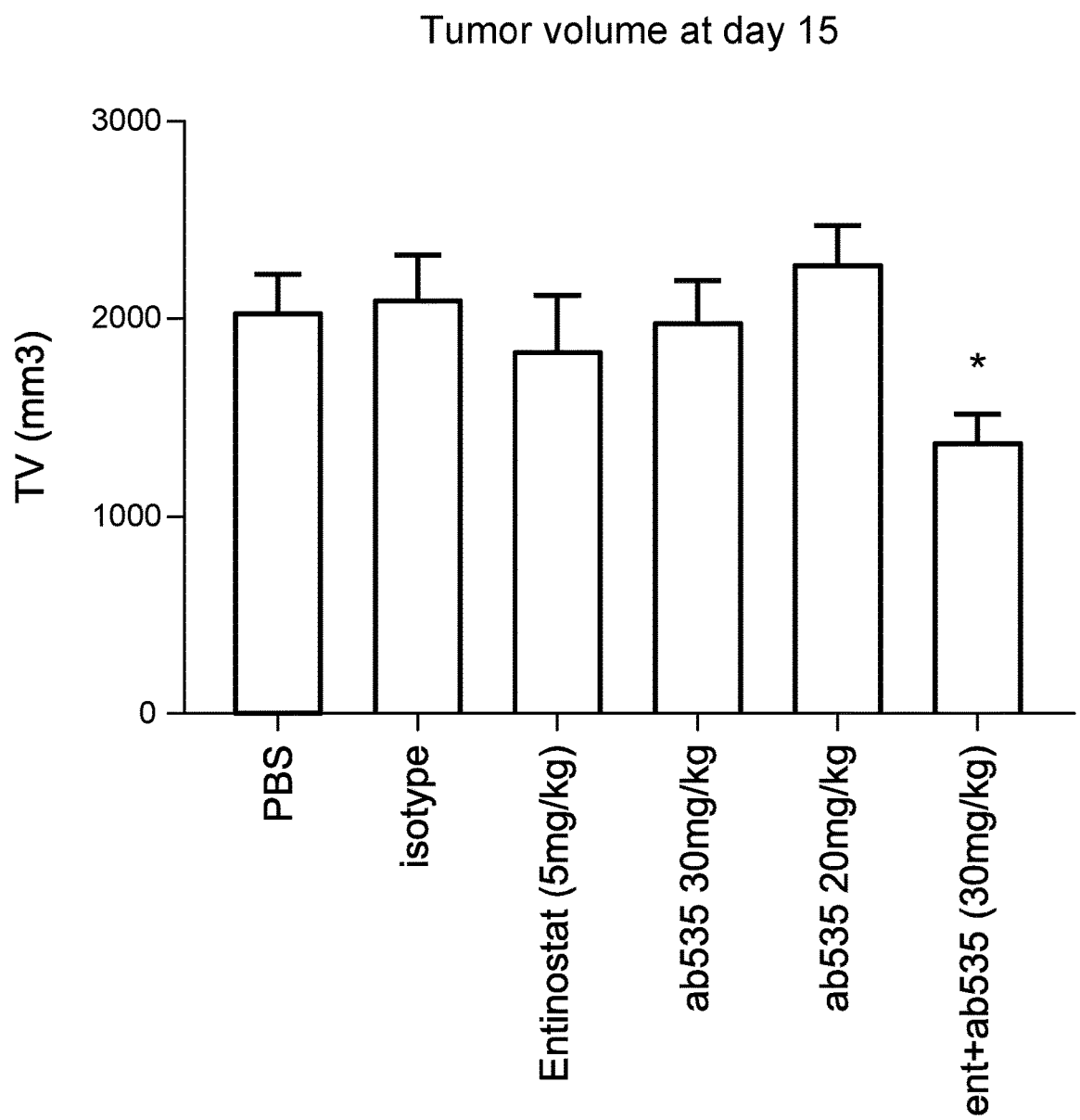
FIG. 2 is a bar graph showing that the combination of entinostat and Ab535 results in tumor growth inhibition at day 15.

To evaluate anti-tumor efficacy, bi-weekly tumor volume measurement were taken in CT26 colon cancer model (n=9). As indicated in the Kaplan-Meir survival curve in FIG. 1, combination of entinostat (5 mg/kg)+Ab535 (30 mg/kg, 3 times per week) therapy improves animal survival when compared to 1) PBS control, 2) Isotype+vehicle control 3) entinostat (5 mg/kg, po, daily), 4) Ab535 (30 mg/kg, ip, 3 times per week), and 5) Ab535 (20 mg/kg, ip, 2 times per week). Results are representative of 6 independent experiments. Similarly in FIG. 2, combination of entinostat (5 mg/kg)+Ab535 (30 mg/kg, 3 times per week) significantly reduced growth at day 15 when compared to all other experimental conditions tested.

Figure 3:
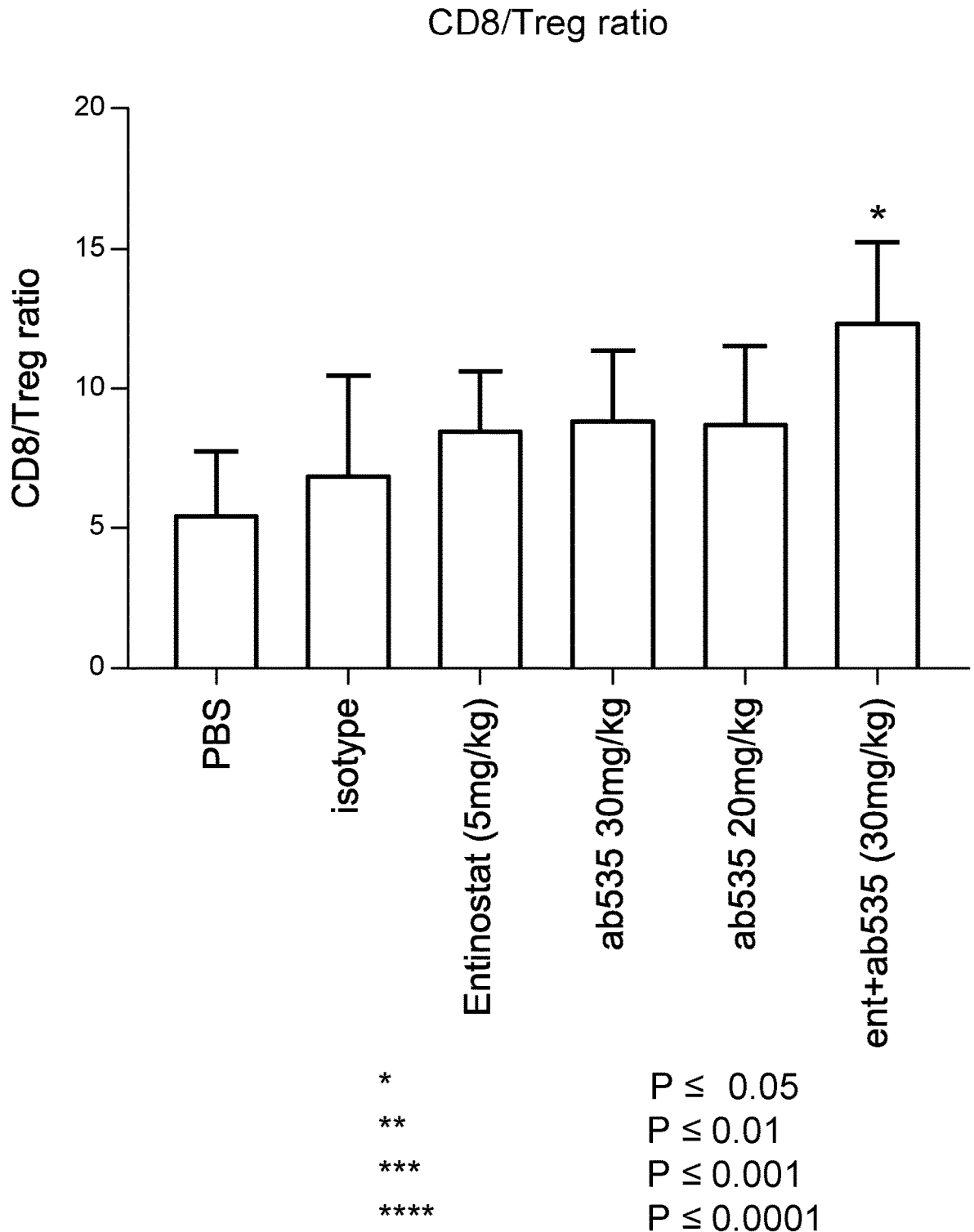
FIG. 3 is a pair of bar graphs showing that the combination of entinostat and Ab535 increases CD8/T-regulatory cell ratio in tumors.
Figure 4:
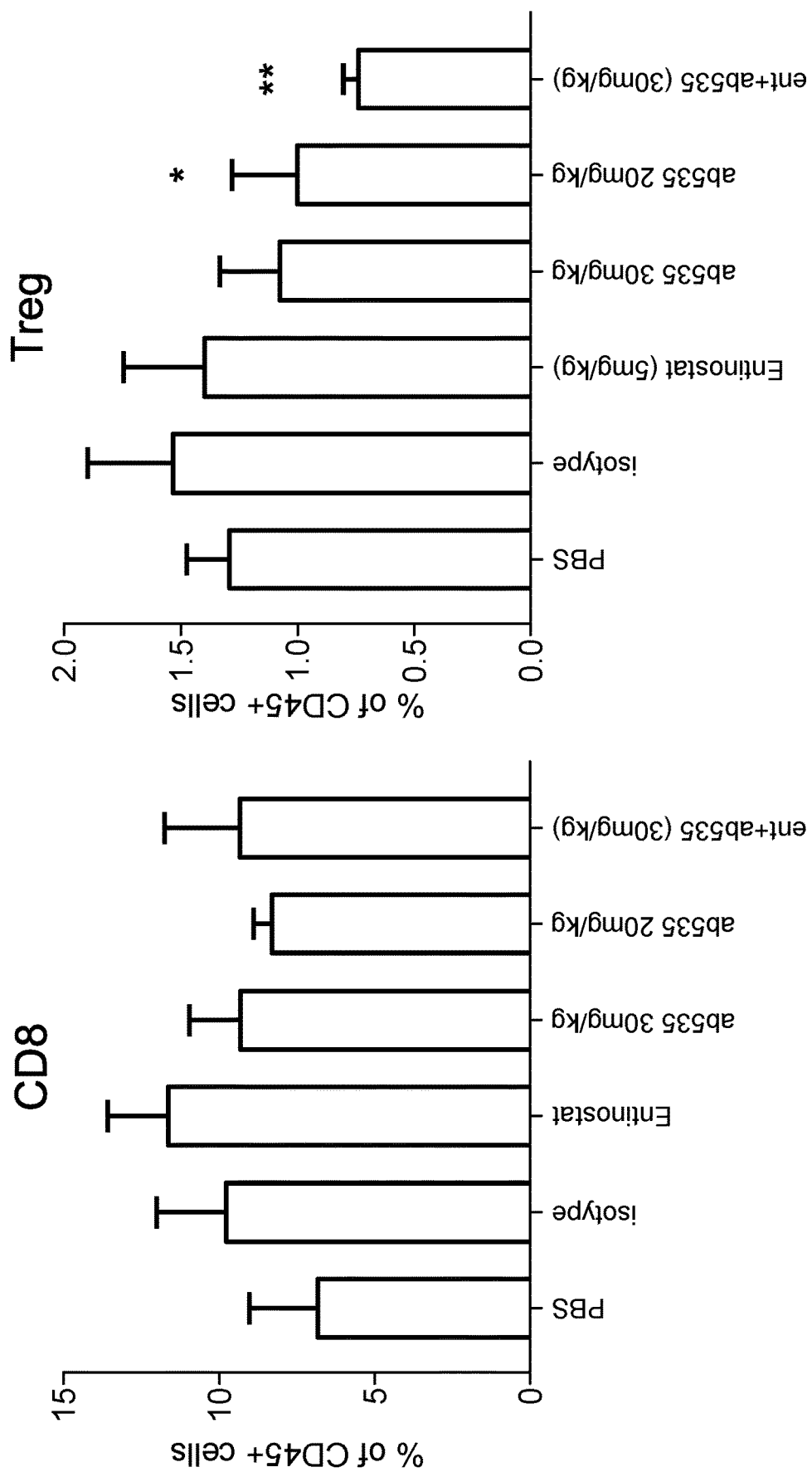
FIG. 4 is a pair of bar graphs showing that the combination of entinostat and Ab535 significantly reduces intratumor T-regulatory cells.
Figure 5:
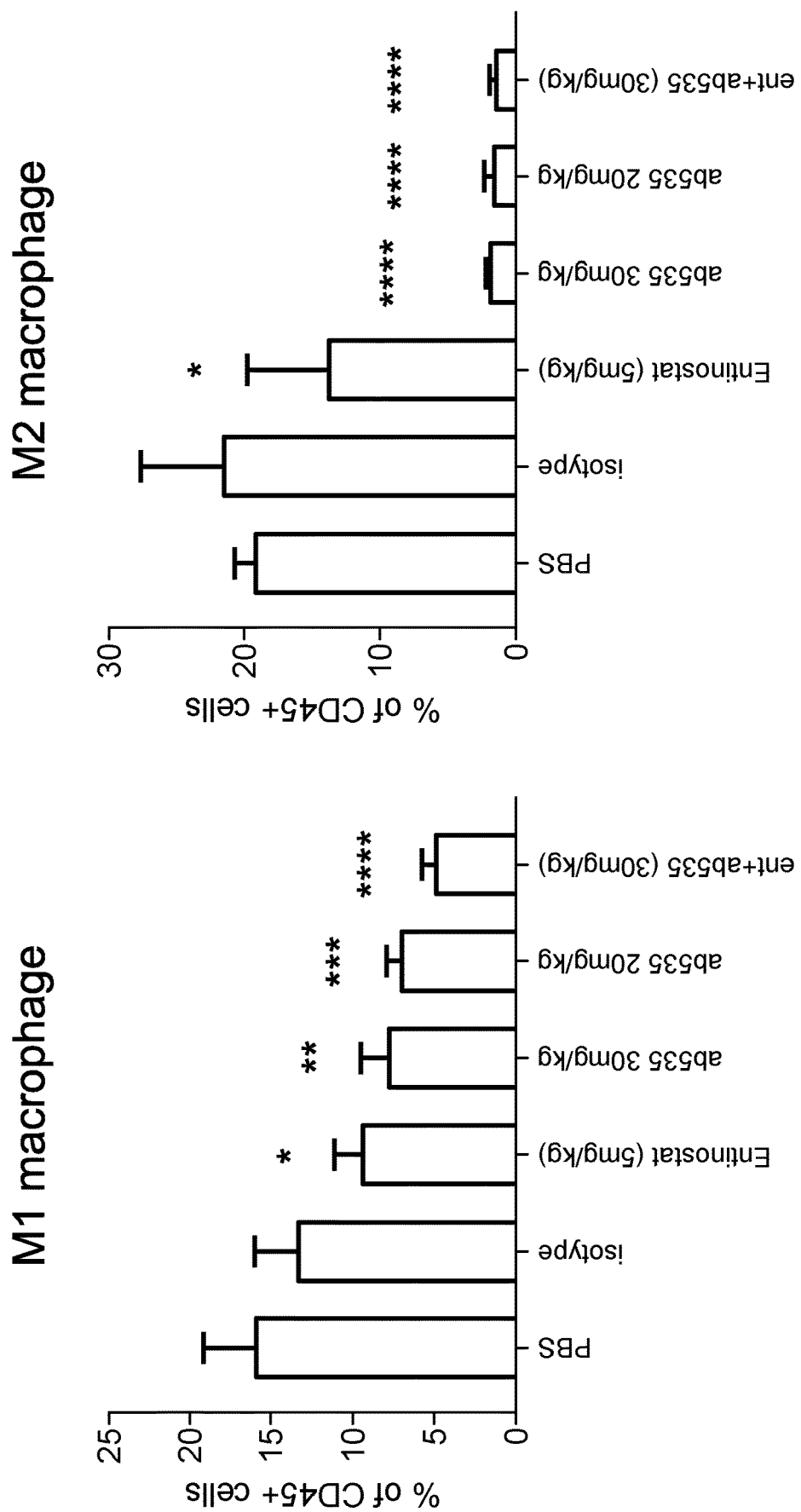
FIG. 5 is a pair of bar graphs showing that the combination of Antibody Ab535 depletes Tumor-associated macrophages (TAM).

To evaluate the tumor immune profile in CT26 colon cancer model (n=4). Tumors were collected at day 8 following treatment with 1) PBS control, 2) Isotype+vehicle control 3) entinostat (5 mg/kg, po, daily), 4) Ab535 (30 mg/kg, ip, 3 times per week), 5) Ab535 (20 mg/kg, ip, 2 times per week), and 6) entinostat (5 mg/kg)+Ab535 (30 mg/kg, 3 times per week). Combination of combination of entinostat (5 mg/kg)+Ab535 (30 mg/kg, 3 times per week) significantly increased the expression of CD8/Treg ratio in tumors when compare to all other experimental conditions (FIG. 3). In FIG. 4, results indicate that combination of entinostat (5 mg/kg)+Ab535 (30 mg/kg, 3 times per week) significantly reduced intra-tumor Treg as well as a significant depletion of tumor-associated macrophages by entinostat (5 mg/kg)+Ab535 (30 mg/kg, 3 times per week) when compare to all other experimental conditions tested in FIG. 5.

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs.

The invention can be embodied in other specific forms without departing from the spirit or essential characteristics thereof. The foregoing description has been presented only for the purposes of illustration and is not intended to limit the invention to the precise form disclosed, but by the claims appended hereto.

---

What is claimed is:

1. A method of treating cancer, wherein the method comprises administering to a patient a combination comprising entinostat and an anti-CSF-1R antibody or an antigen-binding fragment thereof, wherein the anti-CSF-1R antibody or the antigen-binding fragment thereof comprises:

(a) a heavy chain, wherein the variable domain of the heavy chain comprises a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3; and (b) a light chain, wherein the variable domain of the light chain comprises a CDR having the sequence given in SEQ ID NO: 1 for CDR-L1, a CDR having the sequence given in SEQ ID NO:2 for CDR-L2 and a CDR having the sequence given in SEQ ID NO: 3 for CDR-L3.

2. The method of claim 1, wherein
the heavy chain comprises the sequence given in SEQ ID NO:23; and
the light chain comprises the sequence given in SEQ ID NO:15.

3. The method of claim 1, wherein the anti-CSF-1R antibody or the antigen-binding fragment thereof is an antigen-binding fragment selected from the group consisting of a Fab, modified Fab', Fab', F(ab')₂, Fv, VH, VL and scFv fragment.

4. The method of claim 1, wherein the heavy chain comprises the sequence given in SEQ ID NO:27 and the light chain comprises the sequence given in SEQ ID NO:19.

5. The method of claim 1, wherein the inhibitor of CSF-1R activity reduces or blocks the activity of CSF-1R.

6. The method of claim 1, wherein the anti-CSF-1R antibody or the antigen-binding fragment thereof comprises a binding affinity for human CSF-1R of 100 pM or less, or 10 pM or less measured using surface plasmon resonance.

7. The method of claim 1, wherein the cancer is characterized by overexpression of CSF-1R.

8. The method of claim 1, wherein the cancer is colorectal cancer, pancreatic cancer, mesothelioma, glioma, neuroblastoma, ovarian cancer, glioblastoma, myelodysplastic syndromes (MDS), breast cancer, prostate cancer, skin cancer, esophageal cancer, gastric cancer, astrocytic cancer, endometrial cancer, cervical cancer, bladder cancer, renal cancer, lung cancer, liver cancer, thyroid cancer, or head and neck cancer.

9. The method of claim 1, wherein the anti-CSF-1R antibody or the antigen-binding fragment thereof is administered between once every three weeks and four times every week.

10. The method of claim 1, wherein the anti-CSF-1R antibody or the antigen-binding fragment thereof is administered at a dose ranging between about 0.1 mg/kg and about 30 mg/kg.

11. The method of claim 1, wherein the anti-CSF-1R antibody or the antigen-binding fragment thereof is administered at a dose ranging between about 0.1 mg/kg and about 10 mg/kg.

12. The method of claim 1, wherein the anti-CSF-1R antibody or the antigen-binding fragment thereof is administered at a dose of about 0.1 mg/kg, 0.5 mg/kg, 1 mg/kg, 1.5 mg/kg, 3 mg/kg, 5 mg/kg, 6 mg/kg, 7.5 mg/kg, or about 10 mg/kg.

13. The method of claim 1, wherein entinostat is administered orally.

14. The method of claim 1, wherein entinostat is administered once every week at a dose of 5 mg.

15. The method of claim 1, wherein entinostat:
(a) is administered first;
(b) is administered once weekly or twice weekly;
(c) is administered weekly;
(d) is administered every two weeks;
(e) is administered once every week at a dose of 3 mg; or
(f) is administered once every two weeks at a dose of 10 mg.

16. The method of claim 1, wherein entinostat and the anti-CSF-1R antibody or the antigen-binding fragment thereof are administered simultaneously, concurrently or sequentially.

17. The method of claim 1, wherein:
the heavy chain comprises the sequence given in SEQ ID NO:27, wherein the amino acid lysine at position 453 of SEQ ID NO: 27 is missing or deleted, and
the light chain comprises the sequence given in SEQ ID NO:19.

18. The method of claim 1, wherein the cancer is colorectal or pancreatic cancer.

19. A method of treating cancer, wherein the method comprises administering to a patient a synergistic composition of entinostat and an anti-CSF-1R antibody or an antigen-binding fragment thereof, wherein the anti-CSF-1R antibody or the antigen-binding fragment thereof comprises:
(a) a heavy chain comprising the sequence given in SEQ ID NO:23, and wherein the variable domain of the heavy chain comprises a CDR having the sequence given in SEQ ID NO:4 for CDR-H1, a CDR having the sequence given in SEQ ID NO:5 for CDR-H2 and a CDR having the sequence given in SEQ ID NO:6 for CDR-H3; and
(b) a light chain comprising the sequence given in SEQ ID NO:15, and wherein the variable domain of the light chain comprises a CDR having the sequence given in SEQ ID NO: 1 for CDR-L1, a CDR having the sequence given in SEQ ID NO:2 for CDR-L2 and a CDR having the sequence given in SEQ ID NO: 3 for CDR-L3.

20. The method of claim 19, wherein the heavy chain comprises the sequence given in SEQ ID NO:27 and the light chain comprises the sequence given in SEQ ID NO:19.

21. The method of claim 19, wherein the cancer is colorectal cancer, pancreatic cancer, mesothelioma, glioma, neuroblastoma, ovarian cancer, glioblastoma, myelodysplastic syndromes (MDS), breast cancer, prostate cancer, skin cancer, esophageal cancer, gastric cancer, astrocytic cancer, endometrial cancer, cervical cancer, bladder cancer, renal cancer, lung cancer, liver cancer, thyroid cancer, or head and neck cancer.

22. The method of claim 19, wherein the cancer is colorectal or pancreatic cancer.

* * * * *

SEQUENCE LISTING

```
<160> NUMBER OF SEQ ID NOS: 38

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Leu Ala Ser Glu Asp Ile Tyr Asp Asn Leu Ala
1               5                   10

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2
```

```
Tyr Ala Ser Ser Leu Gln Asp
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Leu Gln Asp Ser Glu Tyr Pro Trp Thr
1               5

<210> SEQ ID NO 4
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Ser Leu Thr Thr Tyr Gly Met Gly Val Gly
1               5                   10

<210> SEQ ID NO 5
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Asn Ile Trp Trp Asp Asp Asp Lys Tyr Tyr Asn Pro Ser Leu Lys Asn
1               5                   10                  15

<210> SEQ ID NO 6
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Gly Pro Ile Lys Tyr Pro Thr Ala Pro Tyr Arg Tyr Phe Asp Phe
1               5                   10                  15

<210> SEQ ID NO 7
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Asp Ile Gln Met Thr Gln Ser Pro Ala Ser Leu Ser Ala Ser Leu Gly
1               5                   10                  15
```

```
Glu Thr Val Ser Ile Glu Cys Leu Ala Ser Glu Asp Ile Tyr Asp Asn
             20                  25                  30

Leu Ala Trp Tyr Gln Lys Lys Pro Gly Lys Ser Pro His Leu Leu Ile
         35                  40                  45

Tyr Tyr Ala Ser Ser Leu Gln Asp Gly Val Pro Ser Arg Phe Ser Gly
     50                  55                  60

Ser Gly Ser Gly Thr Gln Tyr Ser Leu Lys Ile Asn Ser Leu Glu Ser
65                  70                  75                  80

Glu Asp Ala Ala Thr Tyr Phe Cys Leu Gln Asp Ser Glu Tyr Pro Trp
                 85                  90                  95

Thr Phe Gly Gly Gly Thr Lys Leu Glu Leu Lys
            100                 105

<210> SEQ ID NO 8
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
gacatccaga tgacacagtc tccagcttcc ctgtctgcat ctctgggaga aactgtctcc     60
atcgaatgtc tagcaagtga ggacatttac gataatttag cgtggtacca agaagaagcca   120 ggaaaatctc ctcacctcct catctattat gcaagtagct tgcaagatgg ggtcccatca   180
cggttcagtg gcagtggatc tggcacacag tattctctca aaatcaacag cctggaatct   240
gaagatgctg cgacttattt ctgtctacag gattctgagt atccgtggac gttcggtgga   300
ggcaccaagc tggaattgaa a                                              321

<210> SEQ ID NO 9
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Gly Val Pro Thr Gln Leu Leu Val Leu Leu Leu Leu Trp Ile Thr
1               5                   10                  15

Asp Ala Ile Cys Asp Ile Gln Met Thr Gln Ser Pro Ala Ser Leu Ser
             20                  25                  30

Ala Ser Leu Gly Glu Thr Val Ser Ile Glu Cys Leu Ala Ser Glu Asp
         35                  40                  45

Ile Tyr Asp Asn Leu Ala Trp Tyr Gln Lys Lys Pro Gly Lys Ser Pro
     50                  55                  60

His Leu Leu Ile Tyr Tyr Ala Ser Ser Leu Gln Asp Gly Val Pro Ser
65                  70                  75                  80

Arg Phe Ser Gly Ser Gly Ser Gly Thr Gln Tyr Ser Leu Lys Ile Asn
                 85                  90                  95

Ser Leu Glu Ser Glu Asp Ala Ala Thr Tyr Phe Cys Leu Gln Asp Ser
            100                 105                 110

Glu Tyr Pro Trp Thr Phe Gly Gly Gly Thr Lys Leu Glu Leu Lys
        115                 120                 125
```

<210> SEQ ID NO 10
<211> LENGTH: 381
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10

```
atgggtgtcc ccactcagct cttggtgttg ttgctgctgt ggattacaga tgccatatgt    60
gacatccaga tgacacagtc tccagcttcc ctgtctgcat ctctgggaga aactgtctcc   120
atcgaatgtc tagcaagtga ggacatttac gataatttag cgtggtacca agaagaagcca  180 ggaaaatctc ctcacctcct catctattat gcaagtagct tgcaagatgg ggtcccatca   240
cggttcagtg gcagtggatc tggcacacag tattctctca aaatcaacag cctggaatct   300
gaagatgctg cgacttattt ctgtctacag gattctgagt atccgtggac gttcggtgga   360
ggcaccaagc tggaattgaa a                                             381
```

<210> SEQ ID NO 11
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Thr Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Asp Lys Tyr Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Leu Thr Asn Val His Thr Ser Asp Ser Ala Thr Tyr Tyr
                85                  90                  95

Cys Ala Arg Ile Gly Pro Ile Lys Tyr Pro Thr Ala Pro Tyr Arg Tyr
            100                 105                 110

Phe Asp Phe Trp Gly Pro Gly Thr Met Val Thr Val Ser
        115                 120                 125
```

<210> SEQ ID NO 12
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
caggttactc tgaaagagtc tggccctggg atattgcagc cctcccagac cctcagtctg    60
acttgcactt tctctgggtt ttcactgacc acttatggta tgggtgtggg ctggattcgt   120
cagccttcag ggaagggtct ggagtggctg gcaaacattt ggtgggatga tgataagtat   180
```

```
tacaatccat ctctgaaaaa ccggctcaca atctccaagg acacctccaa caaccaagca    240
ttcctcaagc tcaccaatgt acacacttca gattctgcca catactactg tgctcggata    300
gggccgatta ataccccgac ggcccccctac cggtactttg acttctgggg cccaggaacc    360
atggtcaccg tctcg                                                     375
```

<210> SEQ ID NO 13
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

```
Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Thr Phe Ser Gly Phe Ser Leu
        35                  40                  45

Thr Thr Tyr Gly Met Gly Val Gly Trp Ile Arg Gln Pro Ser Gly Lys
    50                  55                  60

Gly Leu Glu Trp Leu Ala Asn Ile Trp Trp Asp Asp Lys Tyr Tyr
65                  70                  75                  80

Asn Pro Ser Leu Lys Asn Arg Leu Thr Ile Ser Lys Asp Thr Ser Asn
                85                  90                  95

Asn Gln Ala Phe Leu Lys Leu Thr Asn Val His Thr Ser Asp Ser Ala
            100                 105                 110

Thr Tyr Tyr Cys Ala Arg Ile Gly Pro Ile Lys Tyr Pro Thr Ala Pro
        115                 120                 125

Tyr Arg Tyr Phe Asp Phe Trp Gly Pro Gly Thr Met Val Thr Val Ser
    130                 135                 140
```

<210> SEQ ID NO 14
<211> LENGTH: 432
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14

```
atggacaggc ttacttcctc attcctactg ctgattgtcc ctgcatatgt cctgtctcag     60
gttactctga aagagtctgg ccctgggata ttgcagccct ccagaccct cagtctgact    120 tgcactttct ctgggttttc actgaccact tatggtatgg gtgtgggctg gattcgtcag    180
ccttcaggga agggtctgga gtggctggca aacatttggt gggatgatga taagtattac    240
aatccatctc tgaaaaaccg gctcacaatc tccaaggaca cctccaacaa ccaagcattc    300
ctcaagctca ccaatgtaca cacttcagat tctgccacat actactgtgc tcggataggg    360
ccgattaaat acccgacggc cccctaccgg tactttgact tctggggccc aggaaccatg    420
gtcaccgtct cg                                                        432
```

<210> SEQ ID NO 15
<211> LENGTH: 107
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asp Asn
            20                  25                  30

Leu Ala Trp Tyr Gln Gln Lys Pro Gly Lys Ala Pro Lys Leu Leu Ile
        35                  40                  45

Tyr Tyr Ala Ser Ser Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Asp Ser Glu Tyr Pro Trp
                85                  90                  95

Thr Phe Gly Gly Gly Thr Lys Val Glu Ile Lys
            100                 105

<210> SEQ ID NO 16
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
gacatacaga tgactcagtc accctcaagc ctgagtgcca gtgtgggaga cagggtgaca      60
atcacctgtc tggcctccga ggatatctac gataacctgg catggtatca gcagaaacct    120
ggaaaggctc ccaagctcct gatttattat gcctcctctc tccaagacgg cgttccatct    180
cggttcagcg gaagcggctc cgggacggat tacacactga caattagctc tctgcaaccg    240
gaggattttg ctacttacta ctgcctgcaa gactccgaat acccatggac cttcggtggt    300
ggcaccaaag tggaaatcaa g                                              321

<210> SEQ ID NO 17
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Leu Ala Ser Glu Asp
        35                  40                  45

Ile Tyr Asp Asn Leu Ala Trp Tyr Gln Gln Lys Pro Gly Lys Ala Pro
    50                  55                  60

Lys Leu Leu Ile Tyr Tyr Ala Ser Ser Leu Gln Asp Gly Val Pro Ser
65                  70                  75                  80
```

```
Arg Phe Ser Gly Ser Gly Ser Gly Thr Asp Tyr Thr Leu Thr Ile Ser
            85                  90                  95

Ser Leu Gln Pro Glu Asp Phe Ala Thr Tyr Tyr Cys Leu Gln Asp Ser
            100                 105                 110

Glu Tyr Pro Trp Thr Phe Gly Gly Gly Thr Lys Val Glu Ile Lys
            115                 120                 125

<210> SEQ ID NO 18
<211> LENGTH: 381
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
atgagcgtgc ctactcaagt cttggggctg ctcttgcttt ggcttaccga cgcaagatgc      60
gacatacaga tgactcagtc accctcaagc ctgagtgcca gtgtgggaga cagggtgaca     120
atcacctgtc tggcctccga ggatatctac gataacctgg catggtatca gcagaaacct     180
ggaaaggctc ccaagctcct gatttattat gcctcctctc tccaagacgg cgttccatct     240
cggttcagcg gaagcggctc cgggacggat tacacactga caattagctc tctgcaaccg     300
gaggattttg ctacttacta ctgcctgcaa gactccgaat acccatggac cttcggtggt     360
ggcaccaaag tggaaatcaa g                                                381

<210> SEQ ID NO 19
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asp Asn
            20                  25                  30

Leu Ala Trp Tyr Gln Gln Lys Pro Gly Lys Ala Pro Lys Leu Leu Ile
        35                  40                  45

Tyr Tyr Ala Ser Ser Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Asp Ser Glu Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
              165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
gacatacaga tgactcagtc accctcaagc ctgagtgcca gtgtgggaga cagggtgaca    60
atcacctgtc tggcctccga ggatatctac gataacctgg catggtatca gcagaaacct   120
ggaaaggctc ccaagctcct gatttattat gcctcctctc tccaagacgg cgttccatct   180
cggttcagcg gaagcggctc cgggacggat tacacactga caattagctc tctgcaaccg   240
gaggattttg ctacttacta ctgcctgcaa gactccgaat acccatggac cttcggtggt   300
ggcaccaaag tggaaatcaa gcgtacggta gcggccccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642

<210> SEQ ID NO 21
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Leu Ala Ser Glu Asp
        35                  40                  45

Ile Tyr Asp Asn Leu Ala Trp Tyr Gln Gln Lys Pro Gly Lys Ala Pro
    50                  55                  60

Lys Leu Leu Ile Tyr Tyr Ala Ser Ser Leu Gln Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Leu Gln Asp Ser
            100                 105                 110

Glu Tyr Pro Trp Thr Phe Gly Gly Gly Thr Lys Val Glu Ile Lys Arg
```

```
            115                 120                 125
Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 22
<211> LENGTH: 702
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
atgagcgtgc ctactcaagt cttggggctg ctcttgcttt ggcttaccga cgcaagatgc    60
gacatacaga tgactcagtc accctcaagc ctgagtgcca gtgtgggaga cagggtgaca   120
atcacctgtc tggcctccga ggatatctac gataacctgg catggtatca gcagaaacct   180
ggaaaggctc ccaagctcct gatttattat gcctcctctc tccaagacgg cgttccatct   240
cggttcagcg gaagcggctc cgggacggat tacacactga caattagctc tctgcaaccg   300
gaggattttg ctacttacta ctgcctgcaa gactccgaat acccatggac cttcggtggt   360
ggcaccaaag tggaaatcaa agtacggta gcggccccat ctgtcttcat cttcccgcca   420
tctgatgagc agttgaaatc tggaactgcc tctgttgtgt gcctgctgaa taacttctat   480
cccagagagg ccaaagtaca gtggaaggtg ataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gt                      702
```

<210> SEQ ID NO 23
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Glu Val Thr Leu Lys Glu Ser Gly Pro Ala Leu Val Lys Pro Thr Gln
1               5                  10                  15

Thr Leu Thr Leu Thr Cys Thr Phe Ser Gly Phe Ser Leu Thr Thr Tyr
            20                  25                  30

Gly Met Gly Val Gly Trp Ile Arg Gln Pro Pro Gly Lys Ala Leu Glu
        35                  40                  45
```

```
Trp Leu Ala Asn Ile Trp Trp Asp Asp Lys Tyr Tyr Asn Pro Ser
     50                  55                  60

Leu Lys Asn Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Gly Pro Ile Lys Tyr Pro Thr Ala Pro Tyr Arg Tyr
                100                 105                 110

Phe Asp Phe Trp Gly Gln Gly Thr Met Val Thr Val Ser
            115                 120                 125

<210> SEQ ID NO 24
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
gaagtgacac tcaaggagtc tggacccgct ctggtgaaac caacccaaac actcactttg      60
acatgtactt ttagtggctt ctcattgact acctatggaa tgggcgtggg atggatcaga    120
cagccacctg gcaaggctct ggaatggctg gccaacatct ggtgggatga cgacaagtac    180
tataacccgt ccctgaaaaa ccggctgacc attagcaagg atacttctaa aaatcaagtg    240
gtgctgacca tgacaaatat ggatcccgtt gacaccgcaa cctactactg cgcccgcatt    300
ggtcccataa agtaccctac ggcaccttac cgatatttcg acttttgggg ccaagggaca    360
atggttactg tctcg                                                      375

<210> SEQ ID NO 25
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Met Glu Trp Ser Trp Val Phe Leu Phe Phe Leu Ser Val Thr Thr Gly
 1               5                  10                  15

Val His Ser Glu Val Thr Leu Lys Glu Ser Gly Pro Ala Leu Val Lys
                 20                  25                  30

Pro Thr Gln Thr Leu Thr Leu Thr Cys Thr Phe Ser Gly Phe Ser Leu
             35                  40                  45

Thr Thr Tyr Gly Met Gly Val Gly Trp Ile Arg Gln Pro Pro Gly Lys
     50                  55                  60

Ala Leu Glu Trp Leu Ala Asn Ile Trp Trp Asp Asp Lys Tyr Tyr
 65                  70                  75                  80

Asn Pro Ser Leu Lys Asn Arg Leu Thr Ile Ser Lys Asp Thr Ser Lys
                 85                  90                  95

Asn Gln Val Val Leu Thr Met Thr Asn Met Asp Pro Val Asp Thr Ala
            100                 105                 110

Thr Tyr Tyr Cys Ala Arg Ile Gly Pro Ile Lys Tyr Pro Thr Ala Pro
        115                 120                 125

Tyr Arg Tyr Phe Asp Phe Trp Gly Gln Gly Thr Met Val Thr Val Ser
```

<210> SEQ ID NO 26
<211> LENGTH: 432
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
atggagtggt cctgggtgtt tctgttcttc ctgagtgtga ccaccggggt ccactccgaa    60
gtgacactca aggagtctgg acccgctctg gtgaaaccaa cccaaacact cactttgaca   120
tgtacttta gtggcttctc attgactacc tatggaatgg gcgtgggatg gatcagacag   180
ccacctggca aggctctgga atggctggcc aacatctggt gggatgacga caagtactat   240
aacccgtccc tgaaaaaccg gctgaccatt agcaaggata cttctaaaaa tcaagtggtg   300
ctgaccatga caaatatgga tcccgttgac accgcaacct actactgcgc cgcattggt   360
cccataaagt accctacggc accttaccga tatttcgact ttggggccca agggacaatg   420
gttactgtct cg                                                       432
```

<210> SEQ ID NO 27
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Asp Asp Lys Tyr Tyr Asn Pro Ser
    50                  55                  60

Leu Lys Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Gly Pro Ile Lys Tyr Pro Thr Ala Pro Tyr Arg Tyr
            100                 105                 110

Phe Asp Phe Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
```

```
                195                 200                 205
    Cys Asn Val Asp His Lys Pro Ser Asn Thr Lys Val Asp Lys Arg Val
        210                 215                 220
    Glu Ser Lys Tyr Gly Pro Pro Cys Pro Pro Cys Pro Ala Pro Glu Phe
    225                 230                 235                 240
    Leu Gly Gly Pro Ser Val Phe Leu Phe Pro Pro Lys Pro Lys Asp Thr
                    245                 250                 255
    Leu Met Ile Ser Arg Thr Pro Glu Val Thr Cys Val Val Val Asp Val
                260                 265                 270
    Ser Gln Glu Asp Pro Glu Val Gln Phe Asn Trp Tyr Val Asp Gly Val
            275                 280                 285
    Glu Val His Asn Ala Lys Thr Lys Pro Arg Glu Gln Phe Asn Ser
    290                 295                 300
    Thr Tyr Arg Val Val Ser Val Leu Thr Val Leu His Gln Asp Trp Leu
    305                 310                 315                 320
    Asn Gly Lys Glu Tyr Lys Cys Lys Val Ser Asn Lys Gly Leu Pro Ser
                    325                 330                 335
    Ser Ile Glu Lys Thr Ile Ser Lys Ala Lys Gly Gln Pro Arg Glu Pro
                340                 345                 350
    Gln Val Tyr Thr Leu Pro Pro Ser Gln Glu Glu Met Thr Lys Asn Gln
            355                 360                 365
    Val Ser Leu Thr Cys Leu Val Lys Gly Phe Tyr Pro Ser Asp Ile Ala
    370                 375                 380
    Val Glu Trp Glu Ser Asn Gly Gln Pro Glu Asn Asn Tyr Lys Thr Thr
    385                 390                 395                 400
    Pro Pro Val Leu Asp Ser Asp Gly Ser Phe Phe Leu Tyr Ser Arg Leu
                    405                 410                 415
    Thr Val Asp Lys Ser Arg Trp Gln Glu Gly Asn Val Phe Ser Cys Ser
                420                 425                 430
    Val Met His Glu Ala Leu His Asn His Tyr Thr Gln Lys Ser Leu Ser
            435                 440                 445
    Leu Ser Leu Gly Lys
        450

<210> SEQ ID NO 28
<211> LENGTH: 1966
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
gaagtgacac tcaaggagtc tggacccgct ctggtgaaac caacccaaac actcactttg      60
acatgtactt ttagtggctt ctcattgact acctatggaa tgggcgtggg atggatcaga     120
cagccacctg caaggctct ggaatggctg ccaacatct ggtgggatga cgacaagtac      180
tataacccgt ccctgaaaaa ccggctgacc attagcaagg atacttctaa aaatcaagtg     240
gtgctgacca tgacaaatat ggatcccgtt gacaccgcaa cctactactg cgcccgcatt     300
ggtcccataa agtaccctac ggcaccttac cgatatttcg actttggggg ccaagggaca     360
atggttactg tctcgagcgc ttctacaaag ggcccatccg tcttccccct ggcgccctgc     420
tccaggagca cctccgagag cacagccgcc ctgggctgcc tggtcaagga ctacttcccc     480
gaaccggtga cggtgtcgtg gaactcaggc gccctgacca gcggcgtgca caccttcccg     540
```

-continued

```
gctgtcctac agtcctcagg actctactcc ctcagcagcg tggtgaccgt gccctccagc    600
agcttgggca cgaagaccta cacctgcaac gtagatcaca agcccagcaa caccaaggtg    660
gacaagagag ttggtgagag gccagcacag ggagggaggg tgtctgctgg aagccaggct    720 cagcccctcct gcctggacgc accccggctg tgcagcccca gcccagggca gcaaggcatg   780
ccccatctgt ctcctcaccc ggaggcctct gaccacccca ctcatgccca gggagagggt    840
cttctggatt tttccaccag gctccgggca gccacaggct ggatgcccct accccaggcc    900
ctgcgcatac aggggcaggt gctgcgctca gacctgccaa gagccatatc cggggaggacc   960 ctgcccctga cctaagccca ccccaaaggc caaactctcc actccctcag ctcagacacc   1020
ttctctcctc ccagatctga gtaactccca atcttctctc tgcagagtcc aaatatggtc   1080
ccccatgccc accatgccca ggtaagccaa cccaggcctc gccctccagc tcaaggcggg   1140
acaggtgccc tagagtagcc tgcatccagg acaggcccc agccgggtgc tgacgcatcc    1200
acctccatct cttcctcagc acctgagttc ctgggggggac catcagtctt cctgttcccc   1260
ccaaaaccca aggacactct catgatctcc cggacccctg aggtcacgtg cgtggtggtg   1320
gacgtgagcc aggaagaccc cgaggtccag ttcaactggt acgtggatgg cgtggaggtg   1380
cataatgcca agacaaagcc gcgggaggag cagttcaaca gcacgtaccg tgtggtcagc   1440
gtcctcaccg tcctgcacca ggactggctg aacggcaagg agtacaagtg caaggtctcc   1500
aacaaaggcc tcccgtcctc catcgagaaa accatctcca agccaaagg tgggacccac    1560 ggggtgcgag ggccacatgg acagaggtca gctcggccca ccctctgccc tgggagtgac   1620
cgctgtgcca acctctgtcc ctacagggca gccccgagag ccacaggtgt acaccctgcc   1680
cccatcccag gaggagatga ccaagaacca ggtcagcctg acctgcctgg tcaaaggctt   1740
ctaccccagc gacatcgccg tggagtggga gagcaatggg cagccggaga caactacaa    1800 gaccacgcct cccgtgctgg actccgacgg ctccttcttc ctctacagca ggctaaccgt   1860
ggacaagagc aggtggcagg aggggaatgt cttctcatgc tccgtgatgc atgaggctct   1920
gcacaaccac tacacacaga agagcctctc cctgtctctg ggtaaa                  1966
```

<210> SEQ ID NO 29
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

```
Met Glu Trp Ser Trp Val Phe Leu Phe Leu Ser Val Thr Thr Gly
1               5                   10                  15

Val His Ser Glu Val Thr Leu Lys Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Thr Thr Tyr Gly Met Gly Val Gly Trp Ile Arg Gln Pro Pro Gly Lys
    50                  55                  60

Ala Leu Glu Trp Leu Ala Asn Ile Trp Trp Asp Asp Lys Tyr Tyr
65                  70                  75                  80

Asn Pro Ser Leu Lys Asn Arg Leu Thr Ile Ser Lys Asp Thr Ser Lys
                85                  90                  95
```

Asn Gln Val Val Leu Thr Met Thr Asn Met Asp Pro Val Asp Thr Ala
            100                 105                 110

Thr Tyr Tyr Cys Ala Arg Ile Gly Pro Ile Lys Tyr Pro Thr Ala Pro
            115                 120                 125

Tyr Arg Tyr Phe Asp Phe Trp Gly Gln Gly Thr Met Val Thr Val Ser
130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Lys
            210                 215                 220

Thr Tyr Thr Cys Asn Val Asp His Lys Pro Ser Asn Thr Lys Val Asp
225                 230                 235                 240

Lys Arg Val Glu Ser Lys Tyr Gly Pro Pro Cys Pro Pro Cys Pro Ala
                245                 250                 255

Pro Glu Phe Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser Gln Glu Asp Pro Glu Val Gln Phe Asn Trp Tyr Val
290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
            355                 360                 365

Arg Glu Pro Gln Val Tyr Thr Leu Pro Pro Ser Gln Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
            435                 440                 445

Ser Cys Ser Val Met His Glu Ala Leu His Asn His Tyr Thr Gln Lys
450                 455                 460

Ser Leu Ser Leu Ser Leu Gly Lys
465                 470

<210> SEQ ID NO 30
<211> LENGTH: 2023
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

```
atggagtggt cctgggtgtt tctgttcttc ctgagtgtga ccaccggggt ccactccgaa      60
gtgacactca aggagtctgg acccgctctg gtgaaaccaa cccaaacact cactttgaca     120
tgtactttta gtggcttctc attgactacc tatggaatgg gcgtgggatg gatcagacag     180
ccacctggca aggctctgga atggctggcc aacatctggt gggatgacga caagtactat     240
aacccgtccc tgaaaaaccg gctgaccatt agcaaggata cttctaaaaa tcaagtggtg     300
ctgaccatga caaatatgga tcccgttgac accgcaacct actactgcgc cgcattggt     360
cccataaagt accctacggc accttaccga tatttcgact tttggggcca agggacaatg     420
gttactgtct cgagcgcttc tacaaagggc ccatccgtct tccccctggc gccctgctcc     480
aggagcacct ccgagagcac agccgccctg gctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcacga gacctacac ctgcaacgta gatcacaagc ccagcaacac caaggtggac     720
aagagagttg gtgagaggcc agcacaggga gggagggtgt ctgctggaag ccaggctcag     780
ccctcctgcc tggacgcacc ccggctgtgc agcccagcc cagggcagca aggcatgccc     840
catctgtctc ctcacccgga ggcctctgac cacccacte atgcccaggg agagggtctt     900
ctggattttt ccaccaggct ccgggcagcc acaggctgga tgccctacc ccaggccctg     960
cgcatacagg ggcaggtgct cgctcagac ctgccaagag ccatatccgg gaggaccctg    1020
cccctgacct aagcccaccc caaaggccaa actctccact ccctcagctc agacaccttc    1080
tctcctccca gatctgagta actcccaatc ttctctctgc agagtccaaa tatggtcccc    1140
catgcccacc atgcccaggt aagccaaccc aggcctcgcc ctccagctca aggcgggaca    1200
ggtgccctag agtagcctgc atccagggac aggccccagc cgggtgctga cgcatccacc    1260
tccatctctt cctcagcacc tgagttcctg gggggaccat cagtcttcct gttcccccca    1320
aaacccaagg acactctcat gatctcccgg acccctgagg tcacgtgcgt ggtggtggac    1380
gtgagccagg aagaccccga ggtccagttc aactggtacg tggatggcgt ggaggtgcat    1440
aatgccaaga caaagccgcg ggaggagcag ttcaacagca cgtaccgtgt ggtcagcgtc    1500
ctcaccgtcc tgcaccagga ctggctgaac ggcaaggagt acaagtgcaa ggtctccaac    1560
aaaggcctcc cgtcctccat cgagaaaacc atctccaaag ccaaaggtgg acccacgggg    1620
gtgcgagggc cacatggaca gaggtcagct cggcccaccc tctgccctgg gagtgaccgc    1680
tgtgccaacc tctgtcccta cagggcagcc ccgagagcca caggtgtaca ccctgccccc    1740
atcccaggag gagatgacca agaaccaggt cagcctgacc tgcctggtca aaggcttcta    1800
ccccagcgac atcgccgtgg agtgggagag caatgggcag ccggagaaca actacaagac    1860
cacgcctccc gtgctggact ccgacggctc cttcttcctc tacagcaggc taaccgtgga    1920
caagagcagg tggcaggagg ggaatgtctt ctcatgctcc gtgatgcatg aggctctgca    1980
caaccactac acacagaaga gcctctccct gtctctgggt aaa                      2023
```

<210> SEQ ID NO 31
<211> LENGTH: 107
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 31
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

```
<210> SEQ ID NO 32
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctctcac tttcggcgga   300
gggaccaagg tggagatcaa a                                             321

<210> SEQ ID NO 33
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33
```

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr

```
                    85                  90                  95
Cys Ala Arg Ile Ala Phe Asp Ile Trp Gly Gln Gly Thr Met Val Thr
                100                 105                 110

Val Ser

<210> SEQ ID NO 34
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34
caggtcacct tgaaggagtc tggtcctgcg ctggtgaaac ccacacagac cctcacactg      60
acctgcacct tctctgggtt ctcactcagc actagtggaa tgcgtgtgag ctggatccgt    120
cagcccccag ggaaggccct ggagtggctt gcacgcattg attgggatga tgataaattc    180
tacagcacat ctctgaagac caggctcacc atctccaagg acacctccaa aaaccaggtg    240
gtccttacaa tgaccaacat ggaccctgtg acacagccac gtattactg tgcacggata     300 gcttttgata tctggggcca aggacaatg gtcaccgtct ct                         342

<210> SEQ ID NO 35
<211> LENGTH: 972
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190
```

-continued

```
Leu Lys Val Gln Lys Val Ile Pro Gly Pro Ala Leu Thr Leu Val
        195                 200             205
Pro Ala Glu Leu Val Arg Ile Arg Gly Glu Ala Ala Gln Ile Val Cys
210                 215                 220
Ser Ala Ser Ser Val Asp Val Asn Phe Asp Val Phe Leu Gln His Asn
225                 230                 235                 240
Asn Thr Lys Leu Ala Ile Pro Gln Gln Ser Asp Phe His Asn Asn Arg
                245                 250                 255
Tyr Gln Lys Val Leu Thr Leu Asn Leu Asp Gln Val Asp Phe Gln His
        260                 265                 270
Ala Gly Asn Tyr Ser Cys Val Ala Ser Asn Val Gln Gly Lys His Ser
        275                 280                 285
Thr Ser Met Phe Phe Arg Val Val Glu Ser Ala Tyr Leu Asn Leu Ser
290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
                340                 345                 350
Asn Ala Thr Thr Lys Asp Thr Tyr Arg His Thr Phe Thr Leu Ser Leu
                355                 360                 365
Pro Arg Leu Lys Pro Ser Glu Ala Gly Arg Tyr Ser Phe Leu Ala Arg
        370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
                420                 425                 430
Gln Cys Ser Gly His Thr Asp Arg Cys Asp Glu Ala Gln Val Leu Gln
                435                 440                 445
Val Trp Asp Asp Pro Tyr Pro Glu Val Leu Ser Gln Glu Pro Phe His
450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr His Pro Pro Asp Glu
                500                 505                 510
Phe Leu Phe Thr Pro Val Val Val Ala Cys Met Ser Ile Met Ala Leu
                515                 520                 525
Leu Leu Leu Leu Leu Leu Leu Leu Tyr Lys Tyr Lys Gln Lys Pro
        530                 535                 540
Lys Tyr Gln Val Arg Trp Lys Ile Ile Glu Ser Tyr Glu Gly Asn Ser
545                 550                 555                 560
Tyr Thr Phe Ile Asp Pro Thr Gln Leu Pro Tyr Asn Glu Lys Trp Glu
                565                 570                 575
Phe Pro Arg Asn Asn Leu Gln Phe Gly Lys Thr Leu Gly Ala Gly Ala
                580                 585                 590
Phe Gly Lys Val Val Glu Ala Thr Ala Phe Gly Leu Gly Lys Glu Asp
        595                 600                 605
Ala Val Leu Lys Val Ala Val Lys Met Leu Lys Ser Thr Ala His Ala
```

-continued

```
            610                 615                 620
Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
                675                 680                 685

Pro Gly Gln Asp Pro Glu Gly Gly Val Asp Tyr Lys Asn Ile His Leu
            690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 36
<211> LENGTH: 49
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Met Arg His Thr Asn Tyr Ser Phe Ser Pro Trp His Gly Phe Thr Ile
1               5                   10                  15

His Arg Ala Lys Phe Ile Gln Ser Gln Asp Tyr Gln Cys Ser Ala Leu
            20                  25                  30

Met Gly Gly Arg Lys Val Met Ser Ile Ser Arg Leu Lys Val Gln
        35                  40                  45

Lys
```

<210> SEQ ID NO 37
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
210                 215                 220

Leu Ala Ile His Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
```

-continued

```
                290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
                355                 360                 365

Gly Trp Arg Ala Leu Thr Phe Glu Leu Thr Leu Arg Tyr Pro Pro Glu
                370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
                435                 440                 445

Val Gln Ser Leu Leu Thr Val Glu Thr Leu Glu His Asn Gln Thr Tyr
                450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
                485                 490

<210> SEQ ID NO 38
<211> LENGTH: 512
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
                115                 120                 125

Leu Thr Asp Pro Val Leu Glu Ala Gly Val Ser Leu Val Arg Val Arg
                130                 135                 140

Gly Arg Pro Leu Met Arg His Thr Asn Tyr Ser Phe Ser Pro Trp His
145                 150                 155                 160
```

```
Gly Phe Thr Ile His Arg Ala Lys Phe Ile Gln Ser Gln Asp Tyr Gln
                165                 170                 175
Cys Ser Ala Leu Met Gly Gly Arg Lys Val Met Ser Ile Ser Ile Arg
                180                 185                 190
Leu Lys Val Gln Lys Val Ile Pro Gly Pro Pro Ala Leu Thr Leu Val
                195                 200                 205
Pro Ala Glu Leu Val Arg Ile Arg Gly Glu Ala Ala Gln Ile Val Cys
                210                 215                 220
Ser Ala Ser Ser Val Asp Val Asn Phe Asp Val Phe Leu Gln His Asn
225                 230                 235                 240
Asn Thr Lys Leu Ala Ile Pro Gln Gln Ser Asp Phe His Asn Asn Arg
                245                 250                 255
Tyr Gln Lys Val Leu Thr Leu Asn Leu Asp Gln Val Asp Phe Gln His
                260                 265                 270
Ala Gly Asn Tyr Ser Cys Val Ala Ser Asn Val Gln Gly Lys His Ser
                275                 280                 285
Thr Ser Met Phe Phe Arg Val Val Glu Ser Ala Tyr Leu Asn Leu Ser
290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
                340                 345                 350
Asn Ala Thr Thr Lys Asp Thr Tyr Arg His Thr Phe Thr Leu Ser Leu
                355                 360                 365
Pro Arg Leu Lys Pro Ser Glu Ala Gly Arg Tyr Ser Phe Leu Ala Arg
                370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
                420                 425                 430
Gln Cys Ser Gly His Thr Asp Arg Cys Asp Glu Ala Gln Val Leu Gln
                435                 440                 445
Val Trp Asp Asp Pro Tyr Pro Glu Val Leu Ser Gln Glu Pro Phe His
                450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr His Pro Pro Asp Glu
                500                 505                 510
```